(12) United States Patent
Mikus et al.

(10) Patent No.: US 6,702,846 B2
(45) Date of Patent: Mar. 9, 2004

(54) UROLOGICAL STENT THERAPY SYSTEM AND METHOD

(75) Inventors: Paul W. Mikus, Irvine, CA (US); William G. Moseley, San Diego, CA (US); Jay J. Eum, Irvine, CA (US)

(73) Assignee: Endocare, Inc., Irvine, CA (US)

(*) Notice: Subject to any disclaimer, the term of this patent is extended or adjusted under 35 U.S.C. 154(b) by 0 days.

(21) Appl. No.: 10/091,112

(22) Filed: Feb. 28, 2002

(65) Prior Publication Data

US 2002/0151967 A1 Oct. 17, 2002

Related U.S. Application Data

(63) Continuation-in-part of application No. 09/699,082, filed on Oct. 27, 2000, now Pat. No. 6,416,545, which is a continuation of application No. 09/360,591, filed on Jul. 26, 1999, now Pat. No. 6,139,536, which is a continuation of application No. 09/179,598, filed on Oct. 26, 1998, now Pat. No. 5,928,217, which is a continuation of application No. 08/629,650, filed on Apr. 9, 1996, now Pat. No. 5,830,179, and a continuation-in-part of application No. 09/816,508, filed on Mar. 23, 2001, now Pat. No. 6,629,981, which is a continuation-in-part of application No. 09/612,405, filed on Jul. 6, 2000, now Pat. No. 6,413,269.

(51) Int. Cl.$^7$ ................................................ A61F 2/06
(52) U.S. Cl. ..................................... 623/1.22; 623/1.15
(58) Field of Search .............................. 623/1.15, 1.18, 623/1.19, 1.2, 1.22, 1.12; 606/191–198

(56) References Cited

U.S. PATENT DOCUMENTS

| | | |
|---|---|---|
| 4,170,990 A | 10/1979 | Baumgart et al. |
| 4,490,311 A | 12/1984 | Shepherd |
| 4,503,569 A | 3/1985 | Dotter |
| 4,512,338 A | 4/1985 | Balko et al. |
| 4,553,545 A | 11/1985 | Maass et al. |

(List continued on next page.)

FOREIGN PATENT DOCUMENTS

| | | |
|---|---|---|
| EP | 0 666 065 A1 | 2/1994 |
| EP | 0 626153 A1 | 11/1994 |
| WO | WO 93/13824 | 7/1993 |

OTHER PUBLICATIONS

Pow–Sang, et al., (1995) "Thermaocoagulatin Effect of Diode Laser Radiation in the Human Prostate: Acute and Chronic Study," *Urology* 45(5)790–794.

Cragg, et al., "Percutaneous Arterial Grafting," 150 *Radiology* 45 (Jan. 1984).

(List continued on next page.)

*Primary Examiner*—Kevin T. Truong
(74) *Attorney, Agent, or Firm*—Knobbe, Martens, Olson & Bear, LLP

(57) ABSTRACT

A stent system and method for use in the prostate gland. The stent is made of a shape memory alloy such as nitinol, and has a low temperature martensite state, with a martensite transition temperature below body temperature, and a high temperature austenite state, with an austenite transition temperature at or above body temperature, and a memorized shape in the high temperature austenite state which is a helical coil of diameter large enough to hold the prostatic urethra open. The stent is used to heat the prostate and is left in the prostatic urethra while the prostate heals. After the prostate is substantially healed, the stent is cooled to its martensite state and is easily removed from the urethra.

24 Claims, 21 Drawing Sheets

U.S. PATENT DOCUMENTS

| | | |
|---|---|---|
| 4,733,665 A | 3/1988 | Palmaz |
| 4,762,128 A | 8/1988 | Rosenbluth |
| 4,795,458 A | 1/1989 | Regan |
| 4,913,141 A | 4/1990 | Hillstead |
| 4,969,890 A | 11/1990 | Sugita |
| 5,002,558 A | 3/1991 | Klein et al. |
| 5,019,085 A | 5/1991 | Hillstead |
| 5,037,427 A | 8/1991 | Harada et al. |
| 5,067,975 A | 11/1991 | Jervis |
| 5,078,736 A | 1/1992 | Behl |
| 5,089,005 A | 2/1992 | Harada et al. |
| 5,147,370 A | 9/1992 | McNamara et al. |
| 5,160,341 A | 11/1992 | Brenneman et al. |
| 5,178,618 A | 1/1993 | Kandarpa |
| 5,197,978 A | 3/1993 | Hess |
| 5,224,953 A | 7/1993 | Morgentaler |
| 5,242,451 A | 9/1993 | Harada et al. |
| 5,246,445 A | 9/1993 | Yachia et al. |
| 5,306,294 A | 4/1994 | Winston et al. |
| 5,323,778 A | 6/1994 | Kandarpa |
| 5,366,490 A | 11/1994 | Edwards et al. |
| 5,466,242 A | 11/1995 | Mori |
| 5,514,178 A * | 5/1996 | Torchio ............... 623/1.22 |
| 5,571,135 A | 11/1996 | Fraser et al. |
| 5,601,593 A | 2/1997 | Freitag |
| 5,772,668 A | 6/1998 | Summers et al. |
| 5,776,141 A | 7/1998 | Klein et al. |
| 5,776,142 A | 7/1998 | Gunderson |
| 5,797,952 A | 8/1998 | Klein |
| 5,816,258 A | 10/1998 | Jervis |
| 5,830,179 A | 11/1998 | Mikus et al. |
| 5,928,217 A | 7/1999 | Mikus et al. |
| 6,033,413 A | 3/2000 | Mikus et al. |
| 6,572,648 B1 * | 6/2003 | Klumb et al. ............... 623/1.15 |

OTHER PUBLICATIONS

Terai, et al., "Transurethral Microwave Thermotherapy for BPH," 2 Int. J. Urol 24 (1995).

Soni, et al., Use of Memkath, a Second Generation Urethral Stent for Relief of Urinary Retention in Male Spinal Cord Injured Patients, *Paraplegia* 32 (1994) 480–488.

Poulson, et al., "Memokath: A Second Generation of Intraprostatic Spirals," *British Journal of Urology* (1993) 72, 331–334.

Instent, Prostacoil™, undated brochure.

Harboe, et al., "From Prostakath® to Memokath®," *Stenting the Urinary System*, pp 285–288, publisher/editor unknown, date unknown.

* cited by examiner

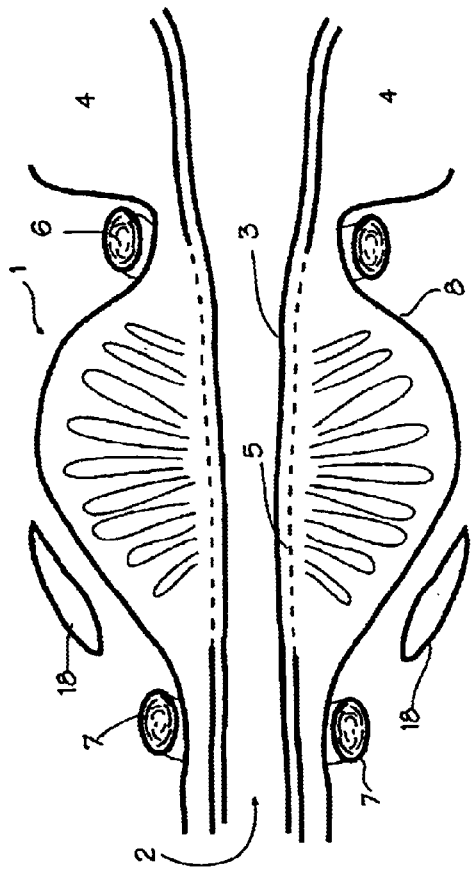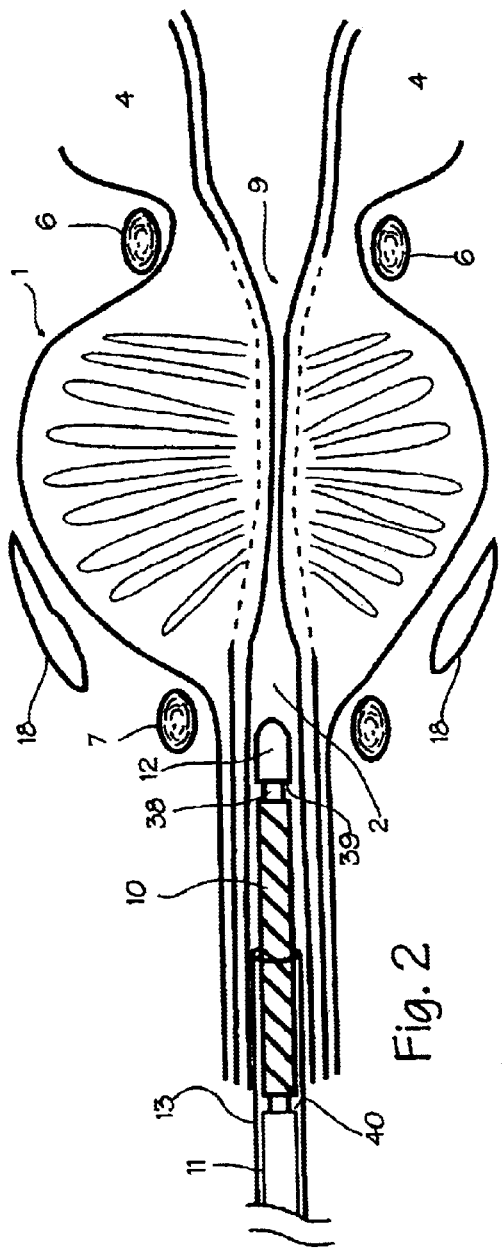

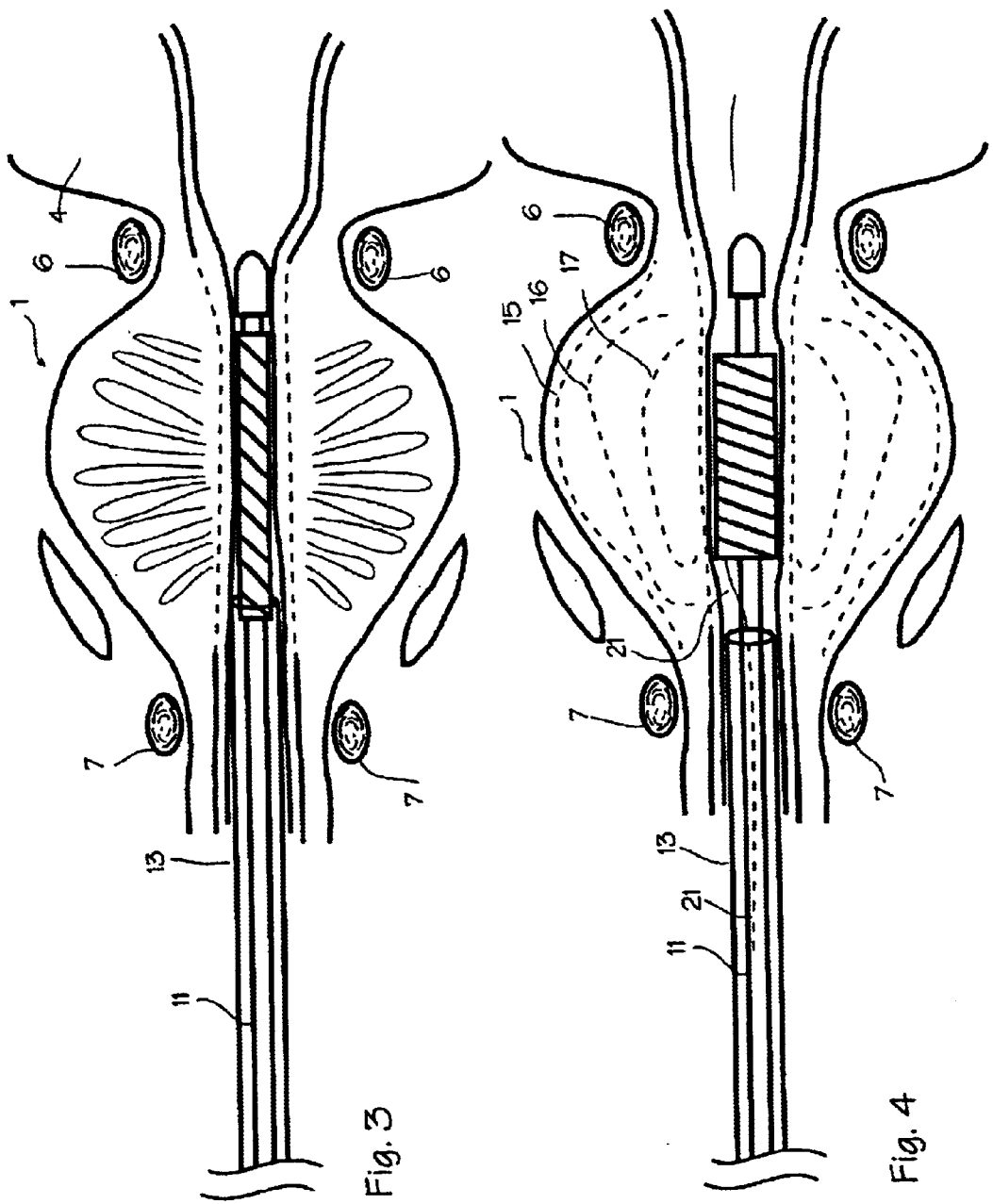

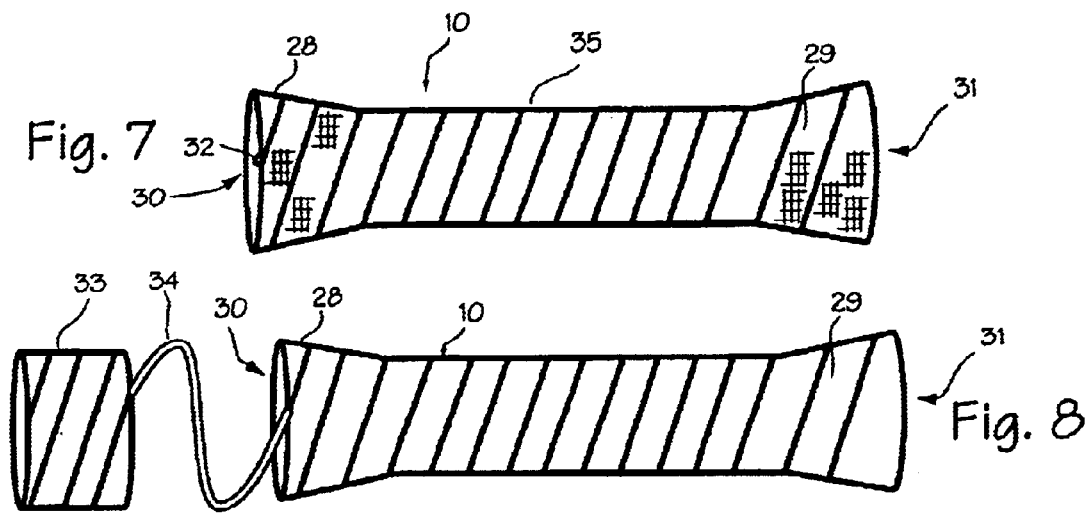
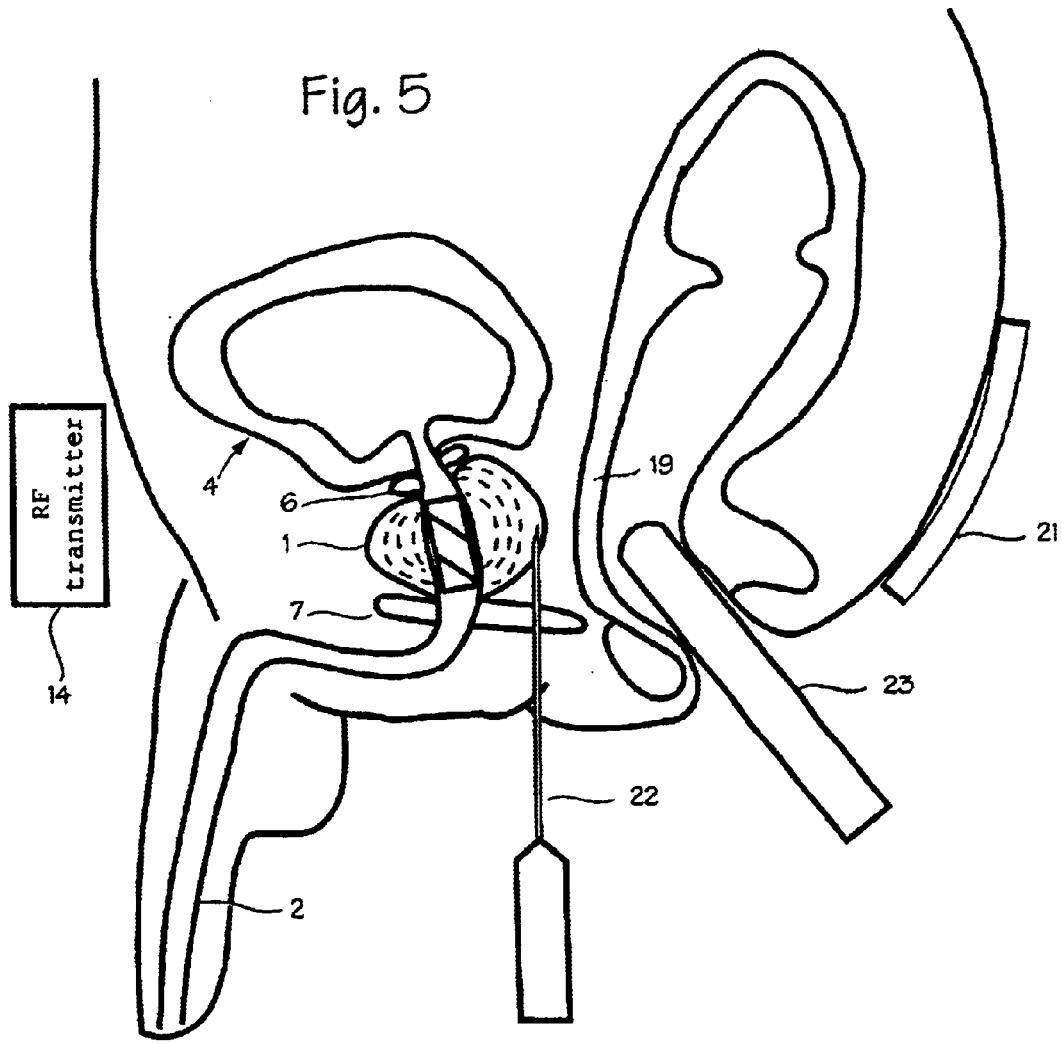

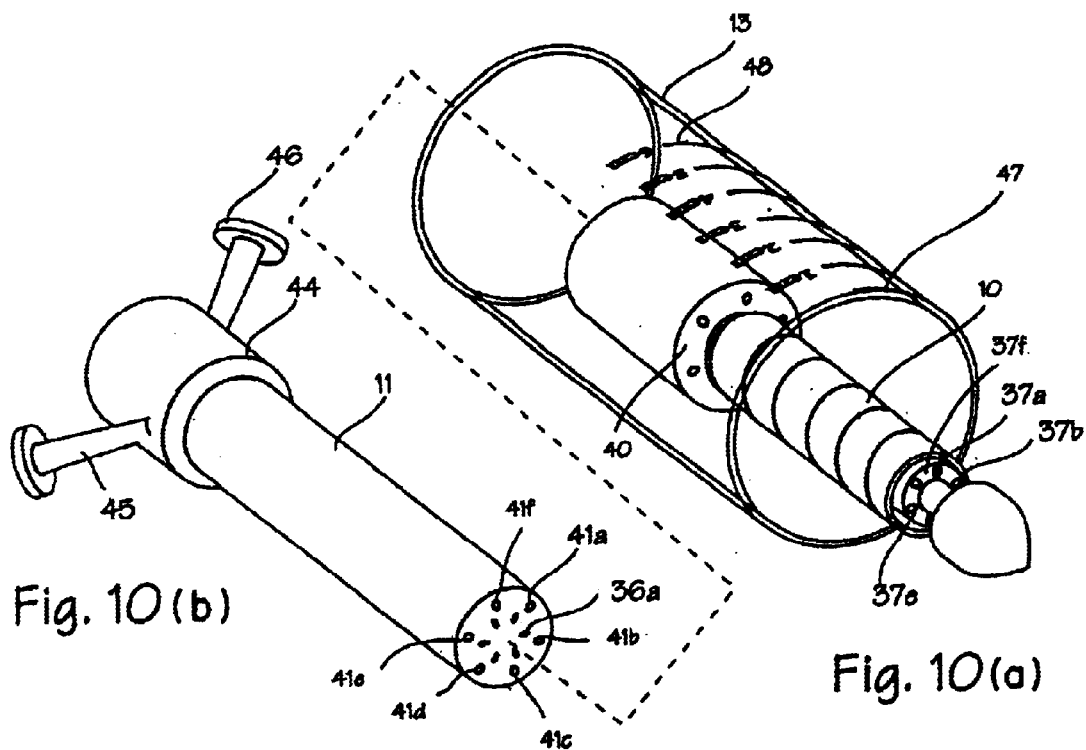
Fig. 10(b)
Fig. 10(a)
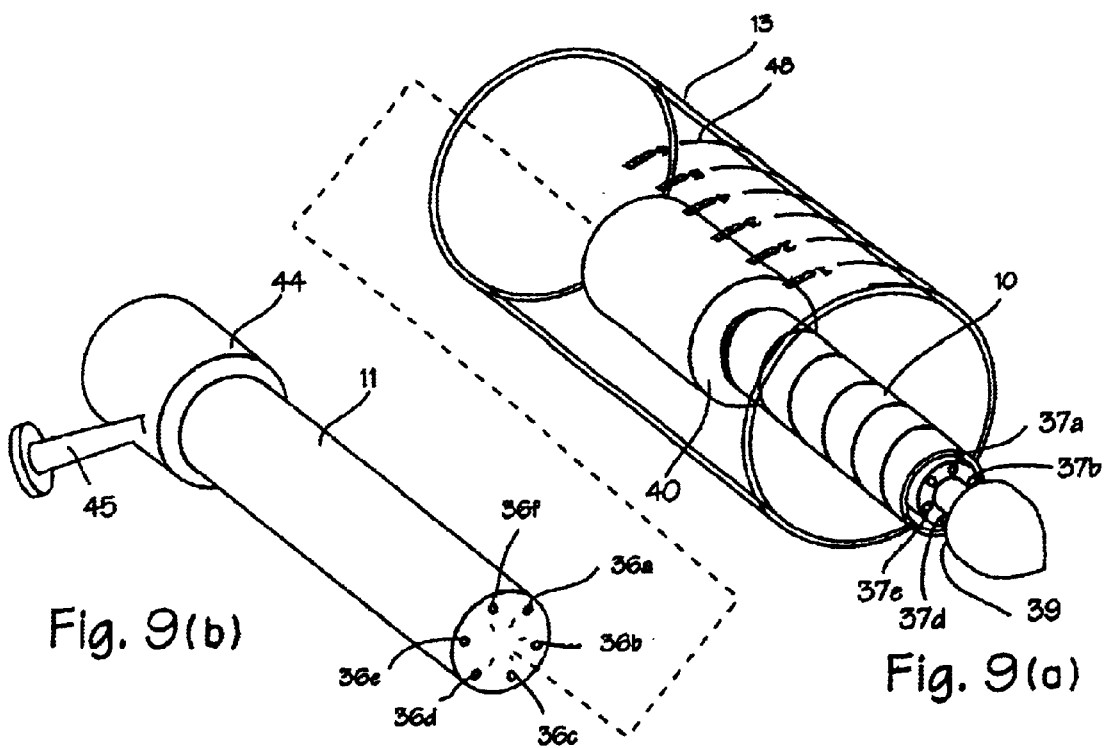
Fig. 9(b)
Fig. 9(a)

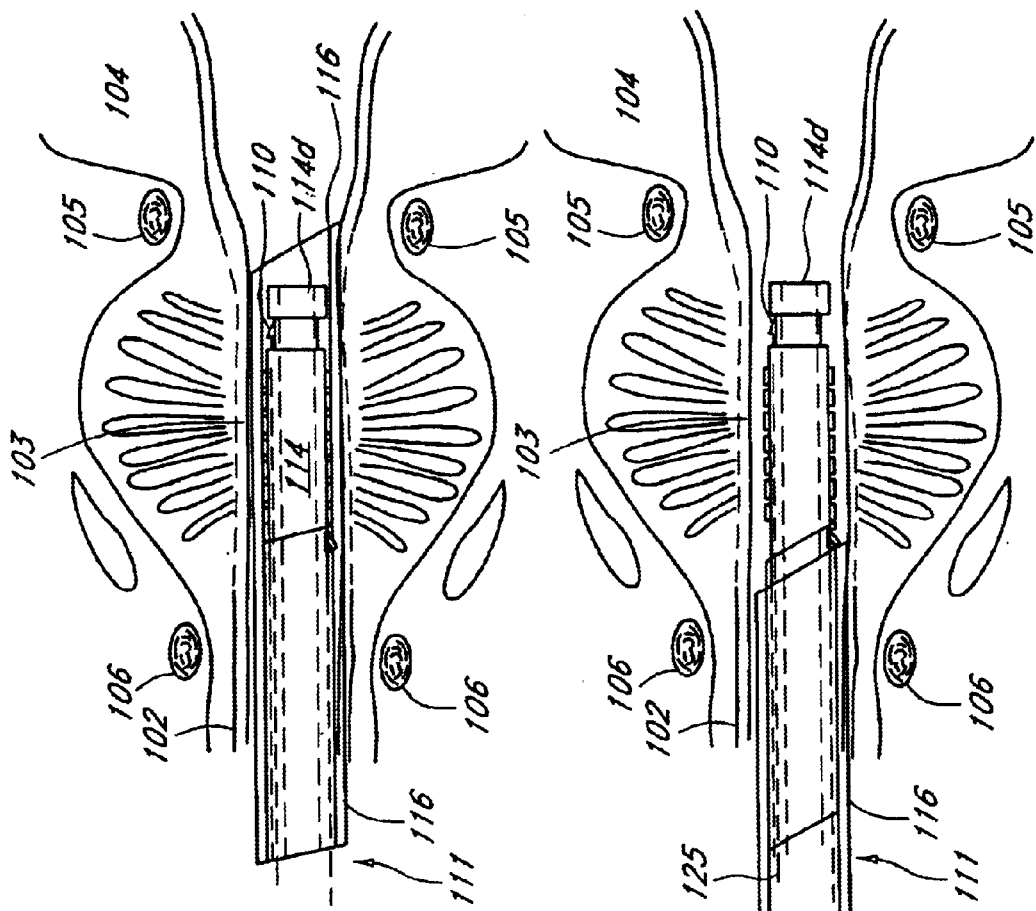

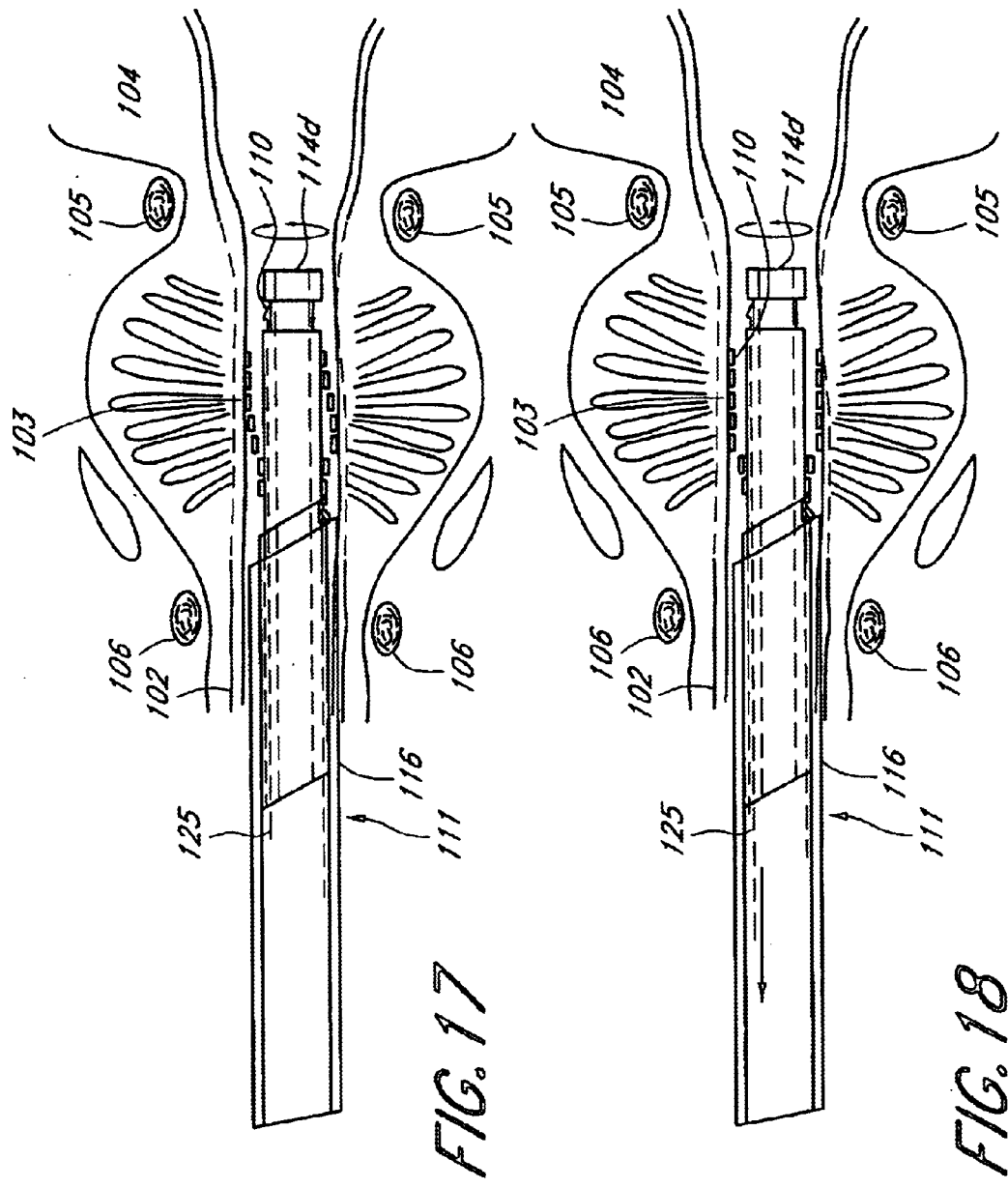

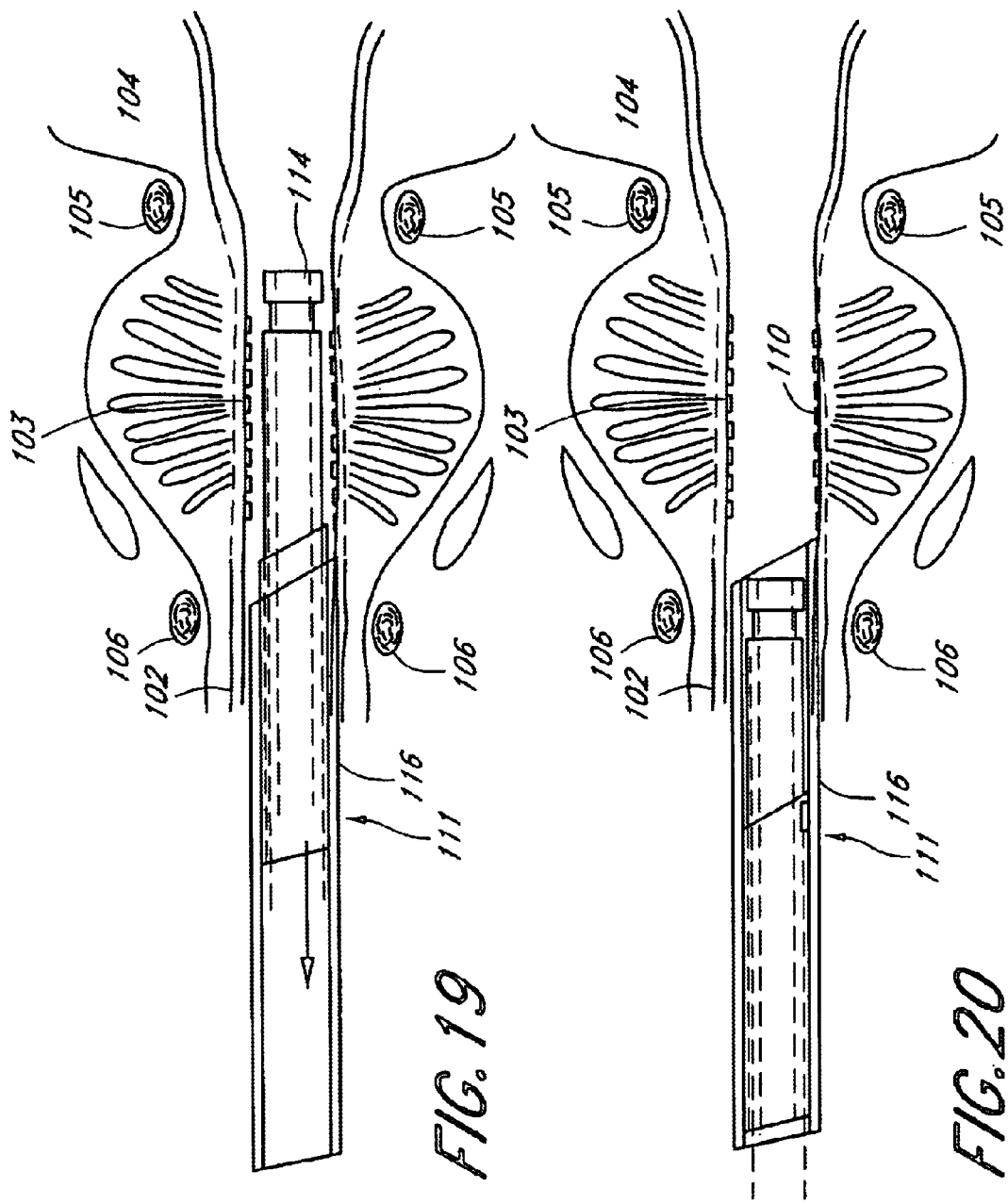

UROLOGICAL STENT THERAPY SYSTEM AND METHOD

CROSS-REFERENCE TO RELATED APPLICATIONS

This application is a continuation-in-part of U.S. application Ser. No. 09/699,082, filed Oct. 27, 2000 now U.S. Pat. No. 6,416,545, which is a continuation of U.S. application Ser. No. 09/360,591, filed Jul. 26, 1999, now U.S. Pat. No. 6,139,536, which is a continuation of U.S. application Ser. No. 09/179,598, filed Oct. 26, 1998, now U.S. Pat. No. 5,928,217, which is a continuation of U.S. application Ser. No. 08/629,650, filed Apr. 9, 1996, now U.S. Pat. No. 5,830,179; and is also a continuation-in-part of U.S. application Ser. No. 09/816,508, filed Mar. 23, 2001 now U.S. Pat. No. 6,629,981, which is a continuation-in-part of U.S. application Ser. No. 09/612,405, filed Jul. 6, 2000 now U.S. Pat. No. 6,413,269. The entirety of each of these applications is hereby incorporated by reference.

BACKGROUND OF THE INVENTION

1. Field of the Invention

Certain embodiments of this invention relate to stents, urology, and treatment for benign prostate hypertrophy or prostate cancer, as well as methods for correction of vessel occlusions.

2. Description of the Related Art

Prostate enlargement, also known as benign prostate hyperplasia or benign prostate hypertrophy, is a common affliction among older men. The condition involves swelling of the prostate. The prostate surrounds the urethra, or urinary tract, and swelling of the prostate prevents passage of urine from the bladder. Benign prostate hyperplasia is uncomfortable because it makes urination difficult or impossible. The condition is also dangerous because it can lead to infection of the bladder and kidneys, and severe cases may lead to death.

Prostate cancer is also a common affliction among older men, and may lead to many of the same symptoms as benign prostate enlargement. Prostate cancer is more dangerous in that it may spread to other organs and is often fatal. Early treatment can reduce the risks of death due to prostate cancer.

A surgical cure for prostate enlargement is called resection. Resection can be accomplished by cutting away a large portion of the prostate gland. The operation can be performed by cutting through the skin to expose the prostate gland, and using scalpels to cut into the prostate. Preferably, resection is accomplished from inside the urethra, using a resectoscope inserted through the penis. The resectoscope includes an endoscope for visual observation and a resecting loop which a surgeon uses to scrape and gouge away the prostate gland from the inside.

Prostate enlargement can be treated with heat treatment such as hyperthermia or thermotherapy, cold treatment (hypothermia or cryotherapy), and ablation. It has long been known that heating a swollen prostate gland can lead to a decrease in swelling and eventual relief from the condition. Heat treatment denaturizes the proteins in the prostate tissue, like a slow cooking of the tissues. The biological effects of heat treatment and the appropriate thermal dosage are discussed in more detail in articles such as Terai, et al., Transurethral Microwave Thermotherapy For Benign Prostatic Hyperplasia, International Journal of Urology 24 (March 1995) and Pow-Sang, et al., Thermocoagulation Effect Of Diode Laser Radiation In The Human Prostate, 45 Urology 790 (May 1995), but it is sufficient for the purposes of this disclosure to understand that application of heat at sufficiently high temperature for sufficient lengths of time to destroy some or all cells in a portion of the prostate gland eventually produces a therapeutic effect.

Devices for heating the prostate are illustrated, for example, in Edwards, et al., Medical Probe Device and Method, U.S. Pat. No. 5,366,490 (Nov. 22, 1994), the entirety of which is hereby incorporated by reference, which shows a device for application of RF or microwave energy into the prostate while protecting the prostatic urethra from damage during the treatment. Hyperthermia treatment, as the term is generally used, is accomplished in the temperature range of 40°–60° C. Thermotherapy, as the term is generally used, is accomplished by heating the prostate above 60° C. Both heat treatments have been beneficially used in the treatment of prostate enlargement.

After heat treatment, the prostate gland will be partially destroyed. Thermal necrosis, thermocoagulation, denaturization, and other such terms are used to describe the thermal damage done to the prostate gland. The prostatic urethra will also be partially destroyed. The prostate gland and the prostatic urethra swell in response to the burn caused by the heat treatment, and this immediately causes acute blockage of the urethra. The prostate gland and prostatic urethra eventually heal, over several weeks or months, typically about three months after heat treatment.

During the healing period, much of the prostate and prostatic urethra that were damaged by the heat treatment are reabsorbed by the body through the blood vessels supplying the area. However, significant portions near the urethra slough off the urethra wall and fall into the urethra. Sloughing causes acute blockage of the urethra. Thus, during the post-operative healing period, swelling and sloughing cause acute blockage of the urethra, leading to extreme discomfort and clinical danger to the patient. After healing, the prostate will be smaller than before heat treatment and will not force closure of the urethra. The condition of benign prostate hyperplasia is essentially cured. Prostate cancer can also be treated successfully with similar heat treatments, usually in combination with chemotherapy or radiation treatment.

It has recently been proposed to use stents to support the urethra and keep it open despite pressure from the swollen prostate. The Prostacoil™ temporary intraprostatic stent, marketed by Instent, Inc. of Eden Prairie, Minn., is an example of a stent adapted for use in the prostatic urethra. The stent includes an anchoring section and a prostatic section, and is placed with a delivery catheter shaft through the urethra. The stent is used long-term, for patients temporarily or permanently unfit for surgery.

A wide variety of stents have been proposed for use in various applications. Intravascular stents and coronary stents such as the Palmaz-Schatz stent illustrated in Palmaz, have been used to treat occlusions of blood vessels. A commonly suggested material for making stents is pseudoelastic and/or shape memory alloys such as nitinol. For example, Sugita, Catheter, U.S. Pat. No. 4,969,890 (Nov. 13, 1990), the entirety of which is hereby incorporated by reference, proposes use of a shape memory alloy for an intravascular stent, and shows a device for percutaneous delivery of the stent to an occluded stenotic region of a blood vessel.

Harada, et al, Method of Implanting a Stent Within a Tubular Organ of a Living Body and of Removing Same, U.S. Pat. No. 5,037,427 (Aug. 4, 1991), the entirety of which is hereby incorporated by reference, proposes use of a two-way shape memory alloy stent in a blood vessel. Two-way shape memory is useful in a stent, according to Harada, to allow removal of the stent. As explained in Harada, it is not possible to remove a one-way shape memory stent after implantation. Harada proposes use of a two-way shape memory stent with a hot, large diameter shape which holds a blood vessel open and a cold, small diameter shape which can be moved within the vessel and removed. Harada also discloses a device for percutaneous placement of the stent.

Dotter, Transluminally Placed Expandable Graft Prosthesis, U.S. Pat. No. 4,503,569, the entirety of which is hereby incorporated by reference, shows the use of a shape memory alloy stent proposed for use in blood vessels. Each of these references use saline solution injected through a catheter to control the temperature of the stent, thereby controlling the shape of the stent.

Stents may be left in blood vessels permanently, and are usually implanted for permanent use. The risk of infection around the stent in a blood vessel, or movement of the stent within a blood vessel, are somewhat limited by the environment. In the urethra, however, the risk of infection is high, and movement within the urethra may be caused by urination or ejaculation, especially if the prostate gland shrinks in response to treatment. Thus, there is a limit to the amount of time a stent may be left implanted in the urethra before infection sets in or migration occurs.

As discussed above, both prostate enlargement and prostate cancer can be treated with heat treatments such as hyperthermia or thermotherapy. As described in U.S. Pat. No. 5,830,179, the entirety of which is hereby incorporated by reference, a stent serves the dual purpose of acting as a heat source for the thermotherapy procedures, as well as acting to hold the urethra open after therapy to prevent blockage due to swelling and prostate tissue sloughing. A stent may be implanted as an interim solution to hold open the urethra while the patient awaits more aggressive surgery or treatment.

A stent may be implanted after hypothermia or cryosurgery to keep the urethra open while enlargement subsides. Finally, a stent may be implanted as a primary treatment. When the stent is implanted for any of these reasons, it is usually better to leave the bladder neck sphincter and the external sphincter unblocked by the stent. These sphincters control the flow of urine through the urethra, and if the stent is placed within these sphincters they will not be able to close. This would leave the patient incontinent. To ensure the proper positioning of the stent, the devices below provide several benefits including controlled release of the stent, tentative initial opening of the stent, and visualization of the bladder and prostatic urethra during placement.

McNamara, et al., Nitinol Stent For Hollow Body Conduits, U.S. Pat. No. 5,147,370 (Sep. 15, 1992), the entirety of which is hereby incorporated by reference, describes a catheter delivery system which uses a single pullwire to retain and release a stent wrapped on the distal end of a catheter. The stent must be provided with "retaining means" in the form of pigtails or hooks on the stent ends capable of engaging a pullwire. The catheter must have two holes communicating into a lumen within the catheter, and the stent ends must enter the lumen through the holes. The pullwire is in the lumen, and engages the stent ends which enter the lumen. After release into the lumen, the retaining means are left to hang in the body lumen. This could lead to thrombus formation in blood vessels and undesirable deposition in urethral stents unless addition precautions are taken to avoid the complications. While materials may be developed in which the stent retaining pigtail structures are not set into the form of the stent, common stent alloys such as Elgiloy, nitinol and stainless steel will take a set in the form of pigtails if deformed as suggested by McNamara.

Hillstead, Apparatus And Method For Placement Of A Stent Within A Subject Vessel, U.S. Pat. No. 4,913,141 (Apr. 3, 1990), the entirety of which is hereby incorporated by reference, discloses a stent delivery device which uses a pullwire running through the central lumen of the catheter and exiting the catheter to run over the stent ends. The stent is deployed by pulling the pullwire proximally, requiring the pullwire to course over intimal and endothelial surfaces of the body lumen to be treated. This could lead to damage of lumenal surfaces and attendant healing responses which are undesirable. Neither McNamara nor Hillstead provide a mechanism which permits retention and release of the stent with a mechanism which remains in the annular space of the stent, and do not present radially extending features such as the radially outwardly protruding pullwires or radially inwardly protruding pigtails.

Othel-Jacobsen, Segmentarily Expandable Tubular Endoluminal Prosthesis, PCT Application No. PCT/DK93/00015, published Jul. 22, 1993 (WO 93/13824), the entirety of which is incorporated by reference, shows a stent which has a primary shape with one or more segments having a diameter which is considerably greater than the rest of the stent. Each segment of the stent has a substantially constant diameter. The larger segments of the stent allow for fastening of the stent inside a natural cavity. However, among other disadvantages, the particular shape of the stent is not always effective in retaining the stent inside the cavity.

SUMMARY OF THE INVENTION

The devices described below include urological stents and devices for placing the stents in the urethra. Methods for treating benign prostate hyperplasia or prostate cancer with heat treatment, either hyperthermia or thermotherapy, using the stent as the heat source, are also described. Also, fabrication of the stent from a nitinol alloy, shape memory alloy, or pseudoelastic alloy, permits easy placement and subsequent removal of the stent, so that the stent may be placed in the urethra during the healing period and removed when no longer necessary. The inventions disclosed and claimed below combine various aspects of treatments discussed above and various new concepts to create new devices and methods for treating benign prostate hyperplasia.

Stent delivery systems described below permit placement of stents in the urethra and other body vessels. The devices are intended to deploy a shape memory stent or other resilient stent into the prostatic urethra under direct vision. The surgeons who use the stent delivery systems can easily place the stent within the prostatic urethra and make sure that the stent does not block the bladder neck sphincter.

In one embodiment, the stent is retained on the catheter with one or more retaining wires or rods which engage the stent ends. The catheter is comprised of two coaxial tubes, one inside the other, and the distal end of the stent is secured to the inner tube while the proximal end of the stent is secured to the outer tube. When both ends of the stent are secured to their respective tubes, the tubes may be rotated relative to each other to open the stent or tighten the stent. The stent may be released from the catheter by pulling the pullwires proximally out of engagement with the stent ends. The pullwire which retains the distal end of the stent may be released first, and the location of the distal end of the stent is observed. Once the distal end of the stent is located properly, the proximal end of the stent may be released from the catheter by pulling the pullwire which retains the proximal end of the stent out of engagement with the proximal end of the stent.

In another embodiment, a stent delivery device includes an inner tube and an outer tube. The inner tube has a distal end releasably connectable to the first end of the stent. The outer tube is rotatably slidable over the inner tube and has a distal end releasably connectable to the second end of the stent. In one embodiment, a sheath is provided which is slideable over the outer tube. A trigger may also be provided which is operably connected to the sheath for moving the sheath along the outer tube. In another embodiment, a belt is operably connected to the outer tube for rotating the outer tube relative to the inner tube. The stent may be releasably connectable to the first and second ends of the stent using at least one pullwire.

In accordance with a further aspect of the present invention, there is provided a stent deployment device. The device comprises a tubular body, having a proximal end and a distal end, the tubular body comprising a first and a second stent support. A hand piece is provided on the proximal end of the tubular body. A first control is provided on the hand piece, for manipulating the first stent support, and a second control is provided on the hand piece for manipulating the second stent support.

In one embodiment, the first stent support comprises an outer tubular sleeve for surrounding the stent. The first control comprises a control for proximally retracting the first stent support, to expose at least a portion of the stent. The first control may comprise a slider switch or lever, such as a trigger.

The second stent support may comprise a tubular body, which is releasably connected to at least a first end of the stent. The second control may comprise a control for rotating the second stent support. In one embodiment, the second control comprises a belt which is wrapped around the second stent support. Lateral retraction of the belt causes a commensurate rotation of the second stent support.

Preferably, the first and second stent supports are concentric tubes, and the stent deployment device further comprises a third stent support, comprising a third tube such that the third stent support forms an inner tube which carries the stent and is releasably connected to a distal end of the stent. The second stent support comprises an intermediate tube, concentrically carried by the inner tube, and releasably secured to a proximal end of the stent. The first stent support comprises an outer tube, concentrically carried by the intermediate tube, for covering the stent during transluminal positioning of the stent deployment device.

Preferably, the third stent support comprises an inside diameter which is greater than the outside diameter of an optical visualization device such as an endoscope which is releasably mounted to the stent deployment device, thereby forming an annular lumen extending distally through the tubular body. An infusion port may be provided on the hand piece, for communication with the annular lumen, to permit infusion of fluid media through the tubular body and out of the distal end thereof.

In another embodiment of the present invention, a stent for use within the prostatic urethra is provided. The stent comprises a length of wire having a substantially helical configuration and being expandable between a collapsed shape and an expanded shape. The expanded shape includes a proximal end and a distal end and a substantially cylindrical portion extending from the distal end toward the proximal end. The expanded shape also includes an enlarged region proximal of the cylindrical portion wherein an outer diameter of the enlarged region progressively increases toward the proximal end.

In another embodiment of the present invention, a method for delivering a stent into the prostatic urethra of a patient is provided. A length of wire is provided having a substantially helical configuration which is expandable between a collapsed shape and an expanded shape. The expanded shape includes a proximal end and a distal end and a substantially cylindrical portion extending from the distal end toward the proximal end. The expanded shape also includes an enlarged region proximal of the cylindrical portion wherein an outer diameter of the enlarged region progressively increases toward the proximal end. The stent is delivered in its collapsed shape into the prostatic urethra of the patient. The stent is expanded to its expanded shape within the prostatic urethra of the patient. The proximal end of the stent is located relatively closer to the external sphincter and the distal end of the stent is located relatively closer to the bladder neck sphincter.

Further features and advantages of the present invention will become apparent from the detailed description of preferred embodiments which follows, when considered together with the attached drawings and claims.

BRIEF DESCRIPTION OF THE DRAWINGS

FIG. 1 is a cross-sectional view of the prostate gland with a stent in place.

FIGS. 2 through 4 are cross sectional views of an enlarged prostate illustrating use of the stent.

FIG. 5 is cross-sectional view of lower abdominal portion of the human body with a stent in place.

FIGS. 7 and 8 are elevational views of the stent, with additional features for use within the prostatic urethra.

FIGS. 9 and 10 are elevational views of a stent delivery catheter for use in accordance with one embodiment of the present invention.

FIG. 15 illustrates initial insertion of a stent delivery system into the prostatic urethra.

FIG. 16 further illustrates the procedure of installing a stent in the prostatic urethra, following retraction of an outer introduction sheath.

FIG. 17 further illustrates the procedure of installing a stent in the prostatic urethra, following partial deployment of the stent.

FIG. 18 further illustrates the procedure of installing a stent in the prostatic urethra, following release of the distal end of the stent.

FIG. 19 further illustrates the procedure of installing a stent in the prostatic urethra, following release of the proximal end of the stent.

FIG. 20 further illustrates the procedure of installing the stent in the prostatic urethra, during proximal retraction of the deployment device.

DETAILED DESCRIPTION OF THE PREFERRED EMBODIMENTS

Figure 6:
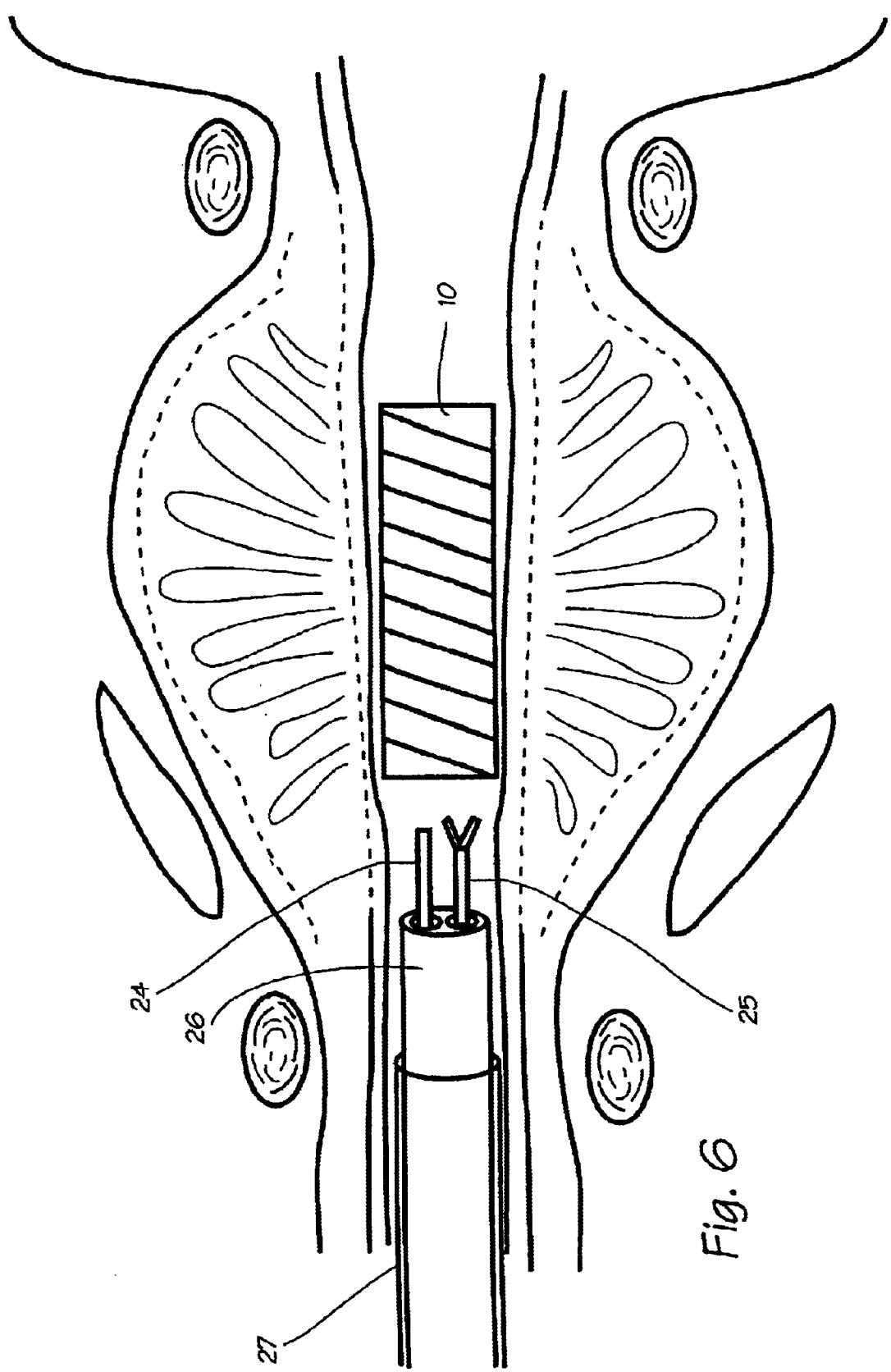
FIG. 6 is a cross-sectional view of the prostate gland with a stent in place and ready for removal.

FIG. 1 shows a stent designed for use in the treatment of benign prostate hyperplasia or prostate cancer. The details of the local anatomy shown in this figure include the prostate gland 1, the urethra 2 and the prostatic urethra 3. The urethra is the channel which conducts urine from the bladder 4 to the penis for discharge from the body. The prostatic urethra is a continuation of the urethra, and it joins the prostate gland to the urethra. The boundary between the prostate gland and the prostatic urethra is ill defined, represented by the dashed line 5. The bladder neck sphincter 6 controls flow of urine from the bladder 4, and the external sphincter 7 controls flow of urine or ejaculate from the bladder 4 or prostate 1. The prostate capsule 8 surrounds the prostate gland. The prostate gland consists of various tissues, including glandular tissue (which produces ejaculate), muscular cells, and epithelial cells. The inside diameter of urethra 2 is typically about 2 centimeters, and the prostatic urethra varies in length from about 15 to 75 mm.

The condition of benign prostate hyperplasia causes the prostate to swell and close off the prostatic urethra, as illustrated in FIG. 2. The urethra 2 is squeezed shut by the swollen prostate, and has an occluded region 9. The stent 10 mounted on the distal portion of delivery catheter 11 with an atraumatic tip 12 is ready for placement in the occluded portion of the prostatic urethra. The stent is made of a nitinol alloy with a martensite transition temperature slightly below body temperature, in the range of about 30°–35° C. (this range is conveniently established or maintained with cold saline flow through the catheter or a catheter sheath). Thus, when the stent is cooled below body temperature by cold saline flow, it will enter the soft and pliable martensite state of the alloy. The chosen alloy has a wide hysteresis, so that it remains in the soft and pliable martensite state for a temperature range distinctly above the temperature at which it converts to martensite upon cooling. The transition temperature for the change to the austenitic state upon heating is slightly above body temperature, in the range of about 38°–60° C., or even higher, depending on the heating source used. When hot saline solution is used, about 38°–60° C. is convenient because that temperature range can be easily achieved by flushing hot saline through the catheter into the vicinity of the stent (100° C. is the equivalent to 212° F., the boiling point of water, so it can be appreciated that the temperature range of about 38°–60° C. is easily achieved in the operating room).

FIG. 2 depicts placement of the stent. The stent pictured in FIG. 2 has been cooled to accomplish the martensite transition, and the stent is soft and pliable. The stent is tightly wound around delivery catheter 11, and has a small diameter of about 1 cm that fits easily into the urethra 2. The catheter sheath 13 is provided to cover the stent during placement and provide a smooth outer surface to facilitate placement of the stent. The stent 10 is then pushed into the occluded region 9 of the prostatic urethra 3, as shown in FIG. 3. Preferably, the stent has an austenite transition temperature above body temperature, and there is no need to flush saline through the delivery catheter or sheath to keep the stent cooled below body temperature. Where the austenite transition temperature is at or below body temperature, the stent should be cooled with cold saline flow to maintain its martensite state until it is properly placed. Alternatively, the stent can be pseudoelastic or superelastic at body temperature, and in this case may be held in its small diameter shape by catheter sheath 13, in which case the sheath serves as a retaining mechanism for the stent.

After placement in a swollen prostate, as depicted in FIG. 3, the stent will be firmly held by the compressive forces of the prostate if swelling is severe enough, which it usually is in cases warranting intervention. Either during or after placement, the stent is flushed with hot saline which causes the stent to heat up above its austenite transition temperature. Of course, if the stent transition temperature is at or below body temperature, it will be sufficient to allow the stent to be heated to the austenite transition temperature by surrounding body temperature without injection of warm saline solution. Upon this transition, the stent recovers its original large diameter shape and forces the prostatic urethra open, as shown in FIG. 4. The stent may be left in the urethra for some time, but eventual infection is almost certain, so that heat therapy is accomplished according to the following description to ensure that the stent is needed for only a short period of time.

To heat the prostate, the stent is used as the heat source. Preferably, radiofrequency energy (RF energy) is broadcast from outside the body, from RF transmitter 14 as illustrated in FIG. 5. RF transmitters available from Valley Labs of Boulder, Colo., capable of transmitting RF energy at powers of up to approximately 300 watts are sufficiently powerful to heat the stent and cause the stent reactively radiate RF energy into the prostate. The hot stent radiates heat into the prostate, and to some extent the reactive radiation from the stent heats prostate tissue. Radiation is maintained for an adequate length of time to heat a large portion of the prostate, indicated by dashed line 15 shown in FIG. 2, to 60° C. or more. FIG. 4 shows dashed line 15, which represents a thermocline of 60° C., and other isotherms of 70° C.

(dashed line 16) and 80° C. (dashed line 17) are shown to illustrate the expected temperature gradient within the prostate during the heat therapy. Typical therapeutic treatments require approximately 10 to 40 minutes with the stent irradiated by 20 to 40 watts of RF energy to create temperatures of at least 40° C. (and preferably 60° C.) in the region to be destroyed. The heating may cause damage to a substantial portion of the prostate, but should avoid damage to surrounding tissues such as the neurovascular bundle 18 shown in FIGS. 1 and 2 and the colon 19 shown in FIG. 5.

During radiation, the stent may be grounded by attaching a ground wire 20 to the stent through the urethra. The ground wire is carried on the delivery catheter, and is releasably attached to the stent or merely in contact with the stent, so that the ground wire may be withdrawn while the stent is left in place. Alternatively, a grounding pad 21 can be placed on the skin near the prostate, providing a ground path through the body to the pad. The heating of the prostate can be monitored with one or more temperature probes 22 inserted through the skin in the transperineal area between the scrotum and the anus. Alternatively, heating may observed via ultrasound imaging through a transrectal ultrasound probe 23. The appearance of healthy and heat damaged prostate tissue may be differentiated on ultrasound images obtained through the ultrasound probe, and the progress of heat therapy can be monitored on the ultrasound displays provided by the ultrasound imaging system associated with the probe. The surgeon performing the therapy will decide when a sufficient portion of the prostate gland has been heat damaged so that eventual re-absorption of that damaged tissue will result in the cure of the condition. As an alternate to direct observation, surgeons may establish standard dosages of RF energy, in terms of wattage, frequency, and time, which ensure adequate heat treatment without danger of damage to surrounding organs, and may be applied without need to monitor thermal damage directly.

Alternate heating means may be employed. For example, the stent may be connected to a DC, AC or radiofrequency source through electrical connections running from the stent, through the delivery catheter, to an external power source. These sources can be used to heat the stent to temperatures sufficient for heat therapy. The same sources may be used for heating the stent to its shape recovery temperature.

After heating via the stent, the heated portion of the prostate gland swells and dies off. The prostatic urethra is also damaged by the treatment and swells and dies. Further occlusion of the urethra is prevented by the stem, which is left in place for some time after heat therapy. While the body's waste removal mechanisms re-absorb the destroyed prostate cells, the stent holds the urethra open and prevents sloughing of dead tissue into the urethra. Over several months, the body will re-absorb the portions of the prostate gland and prostatic urethra damaged by the heat therapy, and the enlargement will subside. During this healing time, the patient has benefited from the stent because it helps avoid the short term closure usually associated with heat therapy.

As the enlargement subsides, the prostate and prostatic urethra will subside from the stent, and the stent will become loose within the urethra. The stent also presents an infection site, and if left in permanently will probably cause infection within the urethra. Thus, when the prostate gland has receded enough that the urethra will be patent upon removal of the stent, and before infection is likely to set in, the stent should be removed. The expected time frame for removal of the stent is two to three months after placement and heat therapy.

Removal of the stent is accomplished by inserting a catheter and flushing the stent with cold saline solution to pause reversion of the dent into the soft, pliable martensite state. As illustrated in FIG. 6, an endoscope 24 and endoscopic graspers 25 are then inserted through a catheter 26 to find and remove the stent. Because the stent is now soft and pliable, typically as easily deformable as silver solder, the stent can be grasped at its proximal end and pulled through the catheter. As the stent is pulled through the catheter, it unravels and deforms to easily fit through the catheter. Alternatively, the grasper can be used to hold the stent in dace while the sheath 27 is gently pushed over the stent. The cold stent is soft and pliable and offers little resistance to the sheath.

When the stent is removed, the urethra is open, and the prostate is almost entirely healed. There may be some residual dead tissue throughout the prostate and the prostatic urethra, but this dead tissue will be removed without incident by the body, either through sloughing, which should occur without ill-effect through the now open urethra, or through continued re-absorption. At this stage, the condition of benign prostate enlargement has been cured.

A number of other features are added to the stent in order to optimize its use within the prostate, as illustrated in FIG. 7. Although destruction of the prostate gland is the desired goal, destruction of surrounding structures is undesirable. The bladder neck sphincter 6 and the external sphincter 7 control urine flow, and damage to these structures would lead to incontinence. To avoid thermal damage to the bladder neck sphincter and the external sphincter, the proximal end 28 and distal end 29 of the stent shown in FIG. 7 are thermally insulated to limit the heat transfer from the stent to the prostate gland at the distal and proximal ends of the stent. Insulating layers of PTFE (Teflon®) or other suitable plastics are sufficient to protect these structures.

The possibility of stent migration can be limited by providing flared ends on the stent. Flared ends 30 and 31 on the stent help to anchor it to the prostate gland and prevent slippage and migration of the stent. A small knob 32 is provided on the proximal end of the stent, attached to the end of the ribbon, and this provides for easier grasping of the stent when it is removed. An optional anchor section 33 and retaining wire 34 can be added to the stent, as shown in FIG. 8. The anchor section is spaced from the stent so that it resided downstream in the urethra and does not obstruct the external sphincter and is not subject to the RF energy used to heat the stent itself. The anchor section may also be thermally and electrically insulated to protect the urethra from any heat that might be conducted from the stent or caused by accidental irradiation from the RF source. The electrical and/or thermal insulation is shown in FIGS. 7 and 8 as the lightly cross hatched areas at either end of the stent.

Typical sizes for the stent are shown in FIG. 7 also. The stent is intended for use in the prostatic urethra 3, which varies in size from man to man. The length of the straight segment 35, when expanded, is about 3–5 cm. The diameter of the straight segment 35, when expanded, is about 2 cm. The length of the flared end portions is about 2 cm, with a diameter of about 3 cm. Thus, the overall length or the stent is about 7 to 9 cm. It may prove desirable to manufacture the stents in just a few standard sizes corresponding to commonly encountered prostate sizes, insofar as an exact size match is not usually necessary. If a non-standard size or an exact size is desired, stents may be specially manufactured to specification. Thus, variations of size beyond the sizes mentioned here may occasionally be needed and accomplished.

The stent will be inserted in its cold state, while it is pliable and easily deformed so that it may be tightly wrapped around the delivery catheter. The catheter diameter may be as small as the state of the art allows, but need only be small enough to fit comfortably into the urethra. Delivery catheter diameter of about 1–1.5 cm with a stent tightly wound around the catheter is sufficiently small to allow easy access with standard catheter insertion techniques. The stent illustrated in the drawings is a ribbon coiled stent. When heated to its high temperature state, the stent takes on the form of a helical coil of flat wire or ribbon, with the successive coils closely spaced, perhaps actually touching, to prohibit intrusion of swollen prostate tissue or sloughing tissue into the prostatic urethra. Closely spaced round wire coils may also be used, and other stent configurations such as expanded metal stents, braided stents and others may also be used.

FIG. 9 illustrates a delivery catheter 11 with the stent 10 tightly wound about the catheter shaft. The catheter is a multi-lumen catheter, with lumens 36a, 36b, 36c, etc. communicating from the proximal end of the catheter to the distal end, with distal outlets 37a, 37b and 37c, etc. With the stent in place around the catheter in the stent recess 38, which is a length of reduced cross section on the catheter between distal retaining shoulder 39 and proximal retaining shoulder 40. Forced flow of warm saline solution out the distal outlets 37 of lumens 36 will warm the stent and cause the distal end of the stent to change to its high temperature memorized shape. As the distal end expands, it will expand against the swollen prostate, and serve to anchor the distal end of the stent, ensuring proper placement of the entire stent whenever the distal end is properly placed. As water diffuses in the prostatic urethra, the more proximal areas of the stent will heat up and revert to the memorized shape, and the stent will expand radially, starting at the distal end and progressing to the proximal end, and thereby anchor itself into the prostatic urethra.

As illustrated in FIG. 10, the injection of saline may also be accomplished proximal end first, by providing additional lumens 41a, 41b, 41c, etc. and lumen outlets 42a, 42b, 42c, etc. in the distal end of the full diameter portion of the delivery catheter. These lumens will provide saline flow to the proximal end of the stent, so that the proximal end will be warmed first, expand and engage the prostate, and anchor the stent from the distal end. (Where an anchor section is provided, the anchor section may be deployed first). In either distal first or proximal first warming, once the end of the stent has expanded so that its diameter is larger than distal retaining shoulder 39 or proximal retaining shoulder 40, the delivery catheter can be moved proximally or distally to place the lumen outlets near unheated portions of the stent, thereby controlling expansion of the stent.

Various clinical factors, including successful visualization of the prostatic urethra, will determine whether a surgeon decides to employ proximal first or distal first deployment. The device may be manufactured to allow for one or the other, or for both simultaneously, or allow selective flow to outlets 37 or 42 during the deployment procedure. In FIG. 9, the proximal end 43 of the delivery catheter is filled with a proximal hub 44 and a luer fitting 45, which provide an input port for saline solution to lumens 36. In FIG. 10, the hub is provide with an additional luer fitting 46 which provides saline flow to the additional lumens which communicate with a coaxial chamber in the hub communicating with proximal outlets of the lumens 41. Where it is desired to provide simultaneous flow paths to both the proximal outlets and the distal outlets, an additional luer fitting is unnecessary and a single chamber within the hub communicating with both sets of lumens 36 and 41 can be provided.

Catheter sheath 13 facilitates placement of the stent. The sheath is transparent and flexible. It is placed inside the urethra over an endoscope. The distal marking 47 is readily visible through the endoscope, as are ruled markings 48. The scope is inserted until the bladder neck sphincter is seen through the scope, and then the catheter sheath is advanced over the scope until the distal marking is visible and placed near the bladder neck sphincter. The endoscope is then pulled back until the external sphincter is located, and the ruled markings on the catheter sheath are used to measure the prostate gland so that a stent of appropriate size can be selected for use. The catheter sheath is left in place while the delivery catheter with a stent tightly wound upon the stent recess is inserted into the urethra through the catheter sheath. An endoscope is inserted either side-by-side with the stent, or within the stent as part of the delivery catheter. When the distal end of the stent is aligned with the desired point of deployment, just inside the prostate, downstream from the bladder neck sphincter, warm saline can be injected to cause expansion and deployment of the distal end of the stent.

Figure 11:
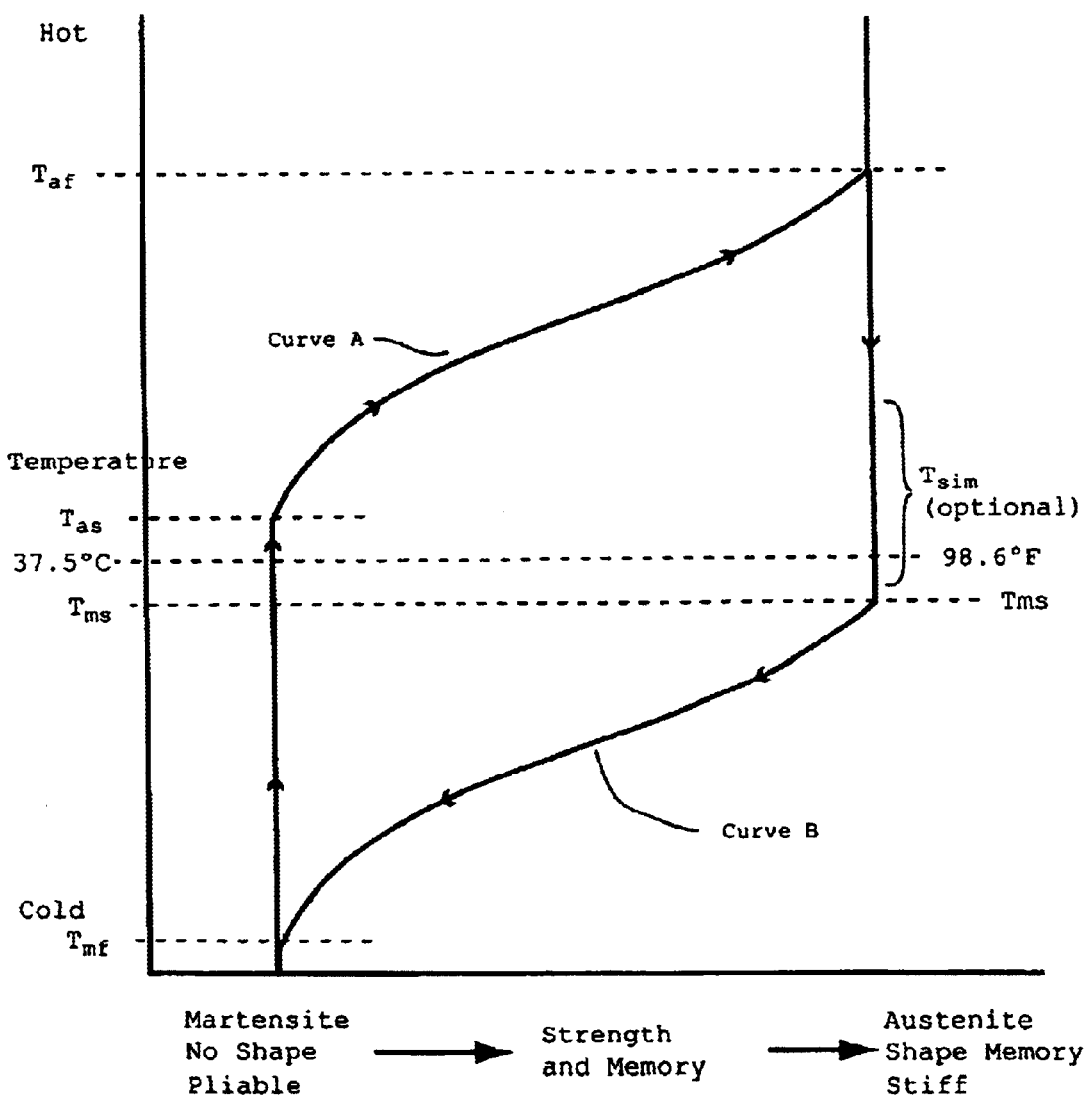
FIG. 11 is a graphical illustration of the stent's behavior in response to temperature changes.

FIG. 11 illustrates the metallurgical behavior of the stent. The stent is made of a shape memory alloy with a martensite state at cold temperature and an austenite state at high temperature, as is characteristic. Nitinol, comprised mostly of nickel and titanium, and usually alloyed with various other metals, is the most common shape memory alloy; however numerous alloys behave in similar fashion. At low temperature, the stent is in its martensite state, and is very pliable and has no memorized shape (except in alloys exhibiting two-way shape memory) and has very little strength. This is shown on the graph on curve A. As temperature rises, at a certain temperature (determined by a variety of factors, including composition of the alloy, readily controlled in the art of shape memory alloys) called the austenite start temperature, $T_{as}$, the metal starts to convert to austenite. The metal becomes stronger, stiffer, and reverts to its memorized shape as temperature increases to $T_{af}$. At the austenite finish temperature, $T_{af}$, the alloy has completely reverted to austenite, has recovered its memorized shape (unless restrained), and is stiff like spring steel. Above $T_{af}$, temperature increases do not affect the behavior of the metal (although it may distemper the metal and destroy its memory). Upon cooling, the metal reverts to the martensite state, but this does not occur exactly in reverse. The temperature at which reversion to martensite occurs upon cooling is lower than the temperature at which martensite-to-austenite conversion occurs. As shown in the graph, upon cooling to the martensite start temperature, $T_{ms}$, which is below body temperature, the metal start to become pliable. Further cooling to the martensite finish temperature $T_{nf}$ results in the complete conversion of the alloy to the soft, pliable martensite state. In the region on curve B above $T_{ms}$, the metal remains stiff and strong, even though the metal was soft and pliable at the same temperature upon heating on Curve A. Thus the alloy must be cooled considerably below the shape memory transition temperature $T_{af}$, before reversion back to the soft martensite state. The behavior is referred to as hysteresis, which is a term which generally refers to delays in changes of states of various systems. In some alloys, superelastic behavior occurs around the region of Curve B above $T_{ms}$. In this region, the metal may be substantially bent (deformed) but still spring back to its memorized shape, and this behavior is markedly different than normal metals. This region is shown on the graph as $T_{sim}$, which varies from alloy to alloy and might not be present in some alloys. Alloys and devices incorporating these characteristics may be manufactured according to known methods in the art of metallurgy.

These characteristics may be employed in the stent as follows. The stent is preferably made with an upward transition temperature (either $T_{as}$, or $T_{af}$) slightly above body temperature. The stent is also made with a downward transition temperature (either $T_{ms}$, or $T_{mf}$) below body temperature. The stent is trained using known techniques to memorize the high temperature shape illustrated above. Thus, once heated to cause the high temperature state with its memorized shape, the stent will remain in that shape at body temperature, and will hold the prostatic urethra open indefinitely. When it is desired to move the stent, cooling the stent with cold saline flow to a temperature below $T_{ms}$ causes it to revert to the cold pliable state, allowing easy deformation so that the stent may be pulled out of the urethra and into a catheter sheath. In alternate embodiments, superelasticity may be incorporated into the stent, so that if the stent is superelastic at body temperature, it may be restrained by the catheter sheath, inserted into the urethra and released by pulling the catheter away from the stent, allowing superelastic reversion to the memorized state. Two-way shape memory stents may also be used, such as those described in Harada, wherein the stent is fabricated to have a memorized shape at high temperature and at low temperature, wherein injection of cold saline around the stent causes reversion to a low temperature memory shape with a small diameter. However, given the expected shrinkage of the prostate gland in response to therapy, the prostate will already be receding from the stent, and it is possible to remove a one-way memory stent in this environment. Thus, two-way shape memory is not necessary in the normal prostatic treatment case.

Figure 12:
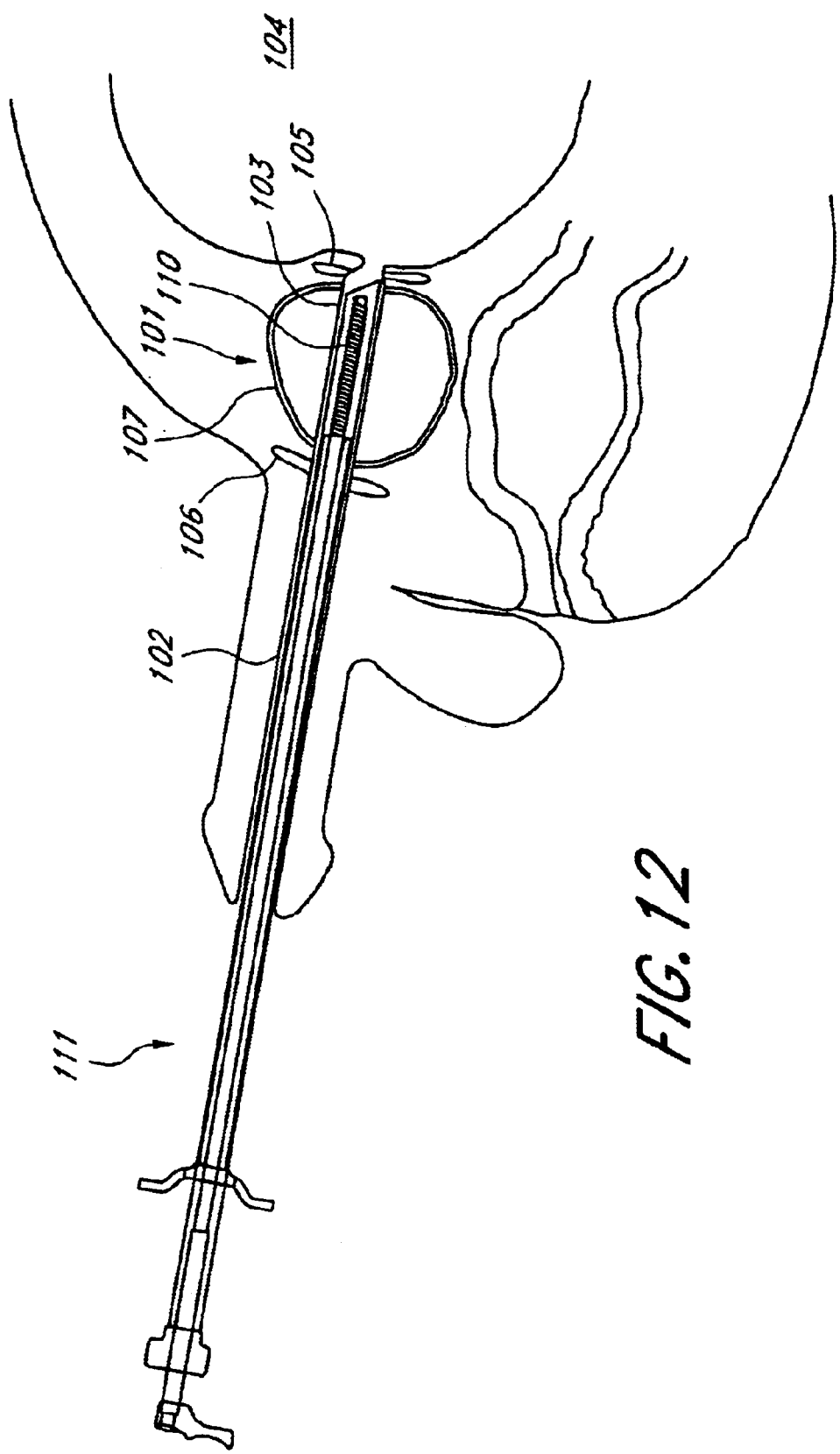
FIG. 12 illustrates a use of a stent delivery system in the treatment of prostate disease in accordance with one embodiment of the present invention.

FIG. 12 shows an overview of a procedure for which a stent and stent delivery system may be used in the treatment of benign prostate hyperplasia or prostate cancer in accordance with one preferred embodiment of the present invention. The details of the local anatomy shown in this figure include the prostate gland 101, the urethra 102 and the prostatic urethra 103. The urethra is the channel which conducts urine from the bladder 104 to the penis for discharge from the body. The prostatic urethra is a continuation of the urethra, and it joins the prostate gland to the urethra. The bladder neck sphincter 105 controls flow of urine from the bladder 104, and the external sphincter 106 controls flow of urine or ejaculate from the bladder 104 or prostate 101. The prostate capsule 107 surrounds the prostate gland. The prostate gland consists of various tissues, including glandular tissue (which produces ejaculate), muscular cells, and epithelial cells. The inside diameter of urethra 102 is typically about 2 centimeters, and the prostatic urethra varies in length from about 15 to 75 mm.

The condition of benign prostate hyperplasia causes the prostate to swell and close off the prostatic urethra. The prostatic urethra 103 is squeezed shut by the swollen prostate, and has an occluded region which must be treated. The stent 110 mounted on the distal portion of delivery catheter 111 is shown ready for placement in the occluded portion of the prostatic urethra. The stent is positioned and released within the prostate through the operation of the delivery catheter as described below. The delivery catheter illustrated in FIG. 12 is rigid, so that the urethra has conformed to the straight configuration of the delivery catheter.

The stent is preferably made of a nitinol alloy with a martensite transition temperature slightly below body temperature, in the range of about 30–35° C. (about 86–95° F.) (this range is conveniently established or maintained with cold saline flow through the catheter or a catheter sheath). Thus, when the stent is cooled below body temperature by cold saline flow, it will enter the soft and pliable martensite state of the alloy. The chosen alloy has a wide hysteresis, so that it remains in the soft and pliable martensite state for a temperature range distinctly above the temperature at which it converts to martensite upon cooling. The transition temperature for the change to the austenitic state upon heating may be varied. It may be just below body temperature, so that warming to body temperature is sufficient to induce reversion to the memorized large diameter configuration. If heating sources are used, the transition temperature may be slightly above body temperature, in the range of about 38–60° C. (about 100–140° F.) or even higher, depending on the heating source used. When hot saline solution is used, about 38–60° C. is convenient because that temperature range can be easily achieved by flushing hot saline through the catheter into the vicinity of the stent (100° C. is the equivalent to 212° F., the boiling point of water, so it can be appreciated that the temperature range of about 38–60° C. is easily achieved in the operating room). Other stent materials may be used in conjunction with the delivery system such as stainless steel, plastics, Elgiloy and other resiliently deformable materials. Even plastically deformable stent materials such as tantalum may be used.

Figure 13:
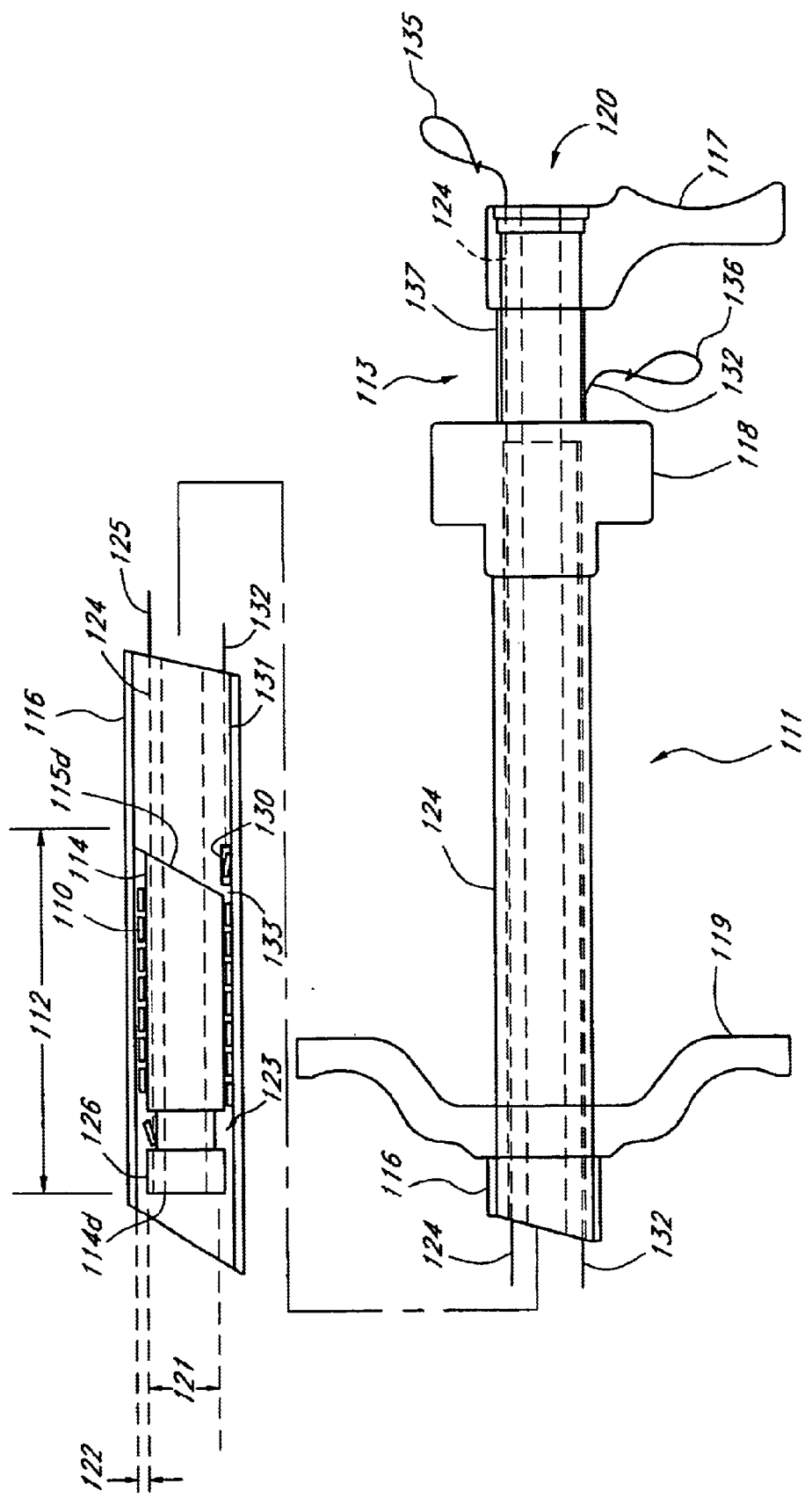
FIG. 13 is a cross section of the stent delivery system of FIG. 12.

FIG. 13 illustrates one stent delivery system. The stent 110 is mounted on the delivery catheter 111 in the distal portion referred to as the stent loading zone 112. The catheter is controlled and the stent is released through operation of the operating mechanism in the proximal end 113 of the delivery catheter. The delivery catheter is comprised of an inner catheter 114 and an outer catheter tube 115 disposed coaxially over the inner catheter, and a sheath 116 coaxially disposed over both the inner catheter and the outer catheter tube. The outer catheter tube and inner catheter are rotatable relative to each other about the longitudinal axis of the catheter, and may be rotated using the proximal handle 117 mounted on the proximal end of the inner catheter and proximal handle 118 mounted on the proximal handle of the outer catheter tube. The inner catheter and outer catheter tube may also slide longitudinally relative to one another. The sheath 116 may also slide relative to the inner catheter and outer catheter tube, and may be operated with the proximal sheath handle 119. The sheath 116 may be rotatable as in the embodiment shown, where no structure inhibits rotation. Alternatively, the sheath may be rotationally fixed relative to either the inner catheter or outer catheter tube, with, or example, a longitudinally oriented tongue and groove structure or spline and keyway structure mating the sheath to the outer catheter tube.

The inner catheter may be a substantially solid cylinder or it may be a hollow tube, in which case it may accommodate an endoscope for viewing the prostatic urethra and stent location before the stent is released. The endoscope lumen 120 shown in FIG. 13 has a diameter approximating common endoscopes. Alternatively, the diameter of lumen 120 may exceed the outside diameter of the scope, to leave an annular channel surrounding the scope for the introduction of saline or other fluid such as to assist in visualization through the scope. The inner catheter, outer catheter and sheath may be made of a transparent plastic or glass so that anatomical landmarks of the prostatic urethra may be seen through the catheter. Medical grade materials, such as stainless steel, may also be used. The components may be rigid, and comprised of stiff transparent plastic such as polyethylene terephthalate (PET) or polycarbonate which facilitates placement in the urethra, but may be made of a flexible transparent or opaque material for placement in other areas of the body where flexibility will facilitate placement. The overall length of the delivery system is generally within the range of about 25 cm to about 50 cm, and in one embodiment, may be about 35 cm (about 14 inches) when constructed for placement of the stent in the urethra.

The outside diameter of the inner catheter diameter 121 at the loading zone 112 is chosen such that, when the stent is wrapped tightly about the distal tip, the overall diameter of the inner catheter and stent is approximately the same as the outer diameter of the outer catheter tube 115. In other words, the inner tube 114 has an outer diameter equal to the outer catheter tube minus twice the stent thickness 122, and the combined inner catheter and stent are isodiametric with the outer catheter tube. The inner diameter of the outer catheter tube is chosen to provide snug but slidable and rotatable fit over the inner catheter, at least near the loading zone. The inner diameter of catheter sheath 116 is chosen to provide snug but slidable and rotatable fit over the outer catheter and stent.

Near the distal tip 114d of the inner catheter 114, an annular recess 123 or notch is formed in the outer wall. The recess or notch does not extend entirely through the catheter wall. In the embodiment shown, the annular recess extends to a depth equal to or greater than the stent thickness. Cut-outs or holes extending entirely through the catheter wall may be used in lieu of the recess or notch. The inner catheter has a side lumen 124 which passes from the distal end of the catheter, at least from the annular recess 123 proximally to the proximal end of the delivery system. The side lumen 124 opens into the annular recess 123. A first pullwire 125, disposed within a side lumen of the inner catheter, extends from the proximal end of the delivery system to the annular recess. The pullwire extends further distally to engage the stent, and, optionally, into the distal extension 126 of the pullwire lumen beyond the annular recess. The pullwire engages a hole 127 or hook in the distal end of the stent (visible in FIG. 14), and thereby retains the distal end of the stent 110 to the distal end 114d inner catheter. The pullwire is preferably sufficiently stiff and rigid to be both pulled and pushed within the pullwire lumen, so that the pullwire may be engaged within the recess to re-engage the stent with the delivery system in order to remove the stent or adjust its position after placement.

Near the distal tip 115d of the outer catheter 115, an annular recess 130 or notch is formed in the outer wall. As with the inner catheter recess, the recess or notch does not extend entirely through the catheter wall. In the embodiment shown, the annular recess extends to a depth equal to or greater than the stent thickness. Cut-out or holes extending entirely through the catheter wall may be used in lieu of the recess or notch. The outer catheter has a side lumen 131 which passes from the distal end of the catheter, at least from the annular recess proximally to the proximal end of the delivery system. The side lumen 131 opens into the annular recess 130. A second pullwire 132, disposed within the side lumen 131 of the outer catheter 115 extends from the proximal end of the delivery system to the annular recess 130. The pullwire 132 extends further distally to engage the stent, and, optionally, into the distal extension 133 of the pullwire lumen beyond the annular recess. The second pullwire 132 engages a hole 134 or hook in the proximal end of the stent (visible in FIG. 14), and thereby retains the proximal end of the stent to the distal end 115d of the outer catheter tube. Again, the pullwire is preferably sufficiently stiff and rigid to be both pulled and pushed within the pullwire lumen, so that the pullwire may be engaged within the recess to engage the stent.

Referring now to the proximal end of the stent delivery catheter, the first and second pullwires exit their respective lumens and terminate in pull rings 135 and 136 which can be used to pull the pullwires proximally. When the pullwires are pulled proximally, the ends of the stent which they hold in the annular recesses are released. Interposed between the inner catheter handle 117 and the outer catheter handle 118 is a collet 137. The collet serves to lock the inner catheter and outer catheters longitudinally in relation to each other until longitudinal movement is desired. When movement is desired, the collet is easily removable, and is provided with a longitudinal slit to permit easy removal by the operator during surgery.

The stent delivery system is assembled by wrapping a helical stent around the distal end of the inner catheter tube 114 and placing the distal end of the stent in the recess of the inner catheter tube and placing the proximal end of the stent in the recess of the outer catheter. Further details regarding suitable stents are provided below. The stent is secured on the stent delivery system by passing the first retaining wire longitudinally through the wall of the inner catheter tube to enter the recess of the inner catheter tube and engage the distal end of the stent within the recess, and then passing a second retaining wire longitudinally through the wall of the outer catheter to enter the recess of the outer catheter and engage the proximal end of the stent within the recess. The sheath is then slipped over the entire assembly. If the stent is a nitinol or shape memory alloy or polymer susceptible to superelastic behavior, it is best to assemble the device while maintaining the stent below the superelastic temperature range or the shape recovery transition temperature.

Figure 14:
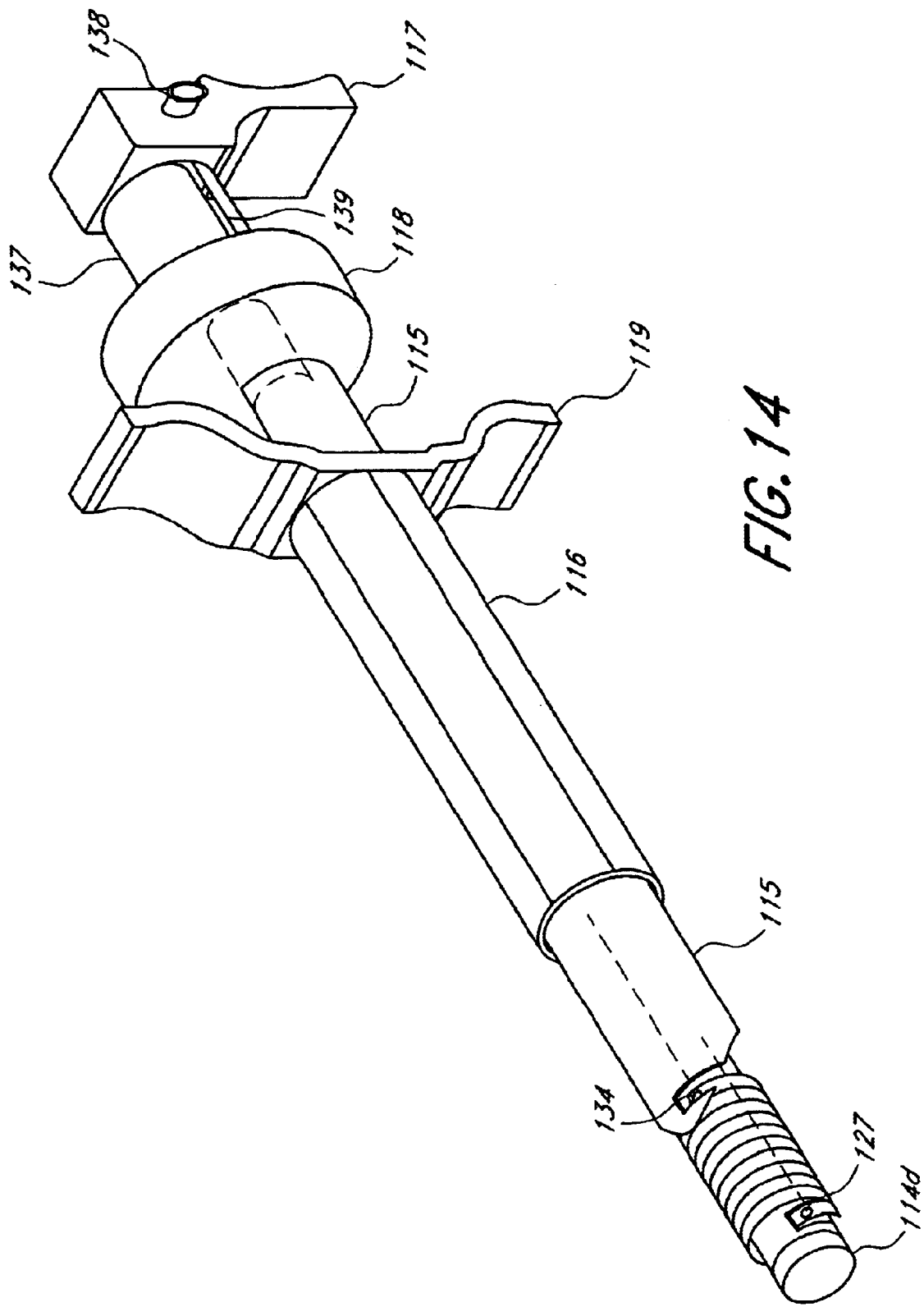
FIG. 14 is a perspective view of the stent delivery system of FIG. 12.

FIG. 14 is a front perspective view of the stent delivery system. In this view, additional features are visible. The proximal handle 117 for the inner catheter tube 114 is fitted with two luer fittings 138 (only one is visible in this view) which permit injection of fluids as required during the procedure. The slit 139 of collet 137 permits easy installation and removal. At the distal end of the delivery catheter, the disposition of the stent distal and proximal end in the recesses 123 and 130 is visible. The pullwires do not need to exit the catheter lumen to engage the stent, and do not pass radially through the catheter wall in order to engage the stent. Additionally, the stent ends to not need to enter the lumen of either the inner catheter or the outer catheter in order to engage with the pullwires, and there is no need for cut-outs in the catheter walls to allow passage of the stent ends into the interior of the catheter. Indeed, the outer catheter lumen is taken up completely by the diameter of the inner catheter, so that the stent ends cannot enter this lumen.

FIGS. 15 through 19 depict placement of the stent. FIG. 15 illustrates initial insertion of the stent delivery system into the prostatic urethra. The surrounding anatomy is shown in a frontal view, and corresponds to the anatomy shown in FIG. 12. The stent has been tightly wound on the stent loading zone of delivery catheter 111, and has a small diameter of about 0.75 to 1 cm (0.25 to 0.40 inches) that fits easily into the urethra 102. When coiled for insertion, the stent is about 4.5 cm (1.75 inches) long. The catheter sheath 116 is provided to cover the stent during placement and provide a smooth outer surface to facilitate placement of the stent. The delivery system is then pushed through the urethra until the stent is located in the prostatic urethra 103, as shown in FIG. 15. An endoscope is placed within the lumen of the inner catheter so that correct initial placement may be verified visually. Preferably, the operator will insert the catheter until the distal end of the sheath is aligned with bladder neck or about 0.25 cm short of the bladder neck. This will locate the stent delivery zone of the catheter between the bladder neck sphincter 105 and the external sphincter 106 inside the prostatic urethra 103.

The next step of the procedure is illustrated in FIG. 16. Having visually confirmed the position of the stent, the operator pulls the sheath 116 proximally until the stent 110 and the distal tip 114d of the inner catheter 114 is exposed. The stent, along with the inner catheter and outer catheter tube, are maintained in position by holding the proximal handles in place while the sheath handle 119 (shown in FIG. 13) is pulled proximally. Next, as illustrated in FIG. 17, the inner catheter 114 is rotated (using the proximal handle 117, shown in FIG. 13) relative to the outer catheter tube 115. This forces the stent to open partially (the proximal and distal ends of the stent are still attached to the delivery system via the pullwires) and partially engage the prostatic urethra 103. The operator may visually confirm the location of the stent and proper opening of the stent through the endoscope. If the stent location is not acceptable, the stent is flushed with cold saline to bring the stent temperature down to the martensite range. This softens the stent, making it pliable and easily re-tightened on the stent loading zone by rotating the inner catheter in the tightening direction. The cold stent is then tightened on the inner catheter by rotating the inner catheter relative to the outer catheter.

When the stent location is acceptable, the distal end of the stent may be released as illustrated in FIG. 18. The pullwire 125 in the inner catheter is pulled proximally and out of engagement with the distal end of the stent. The distal end of the stent is then released to engage the prostatic urethra. Again, the position of the stent may be visually checked through the endoscope, by viewing through the inner catheter wall. If the stent is not properly located, it is preferable to cool it with cold saline to soften, it pull it into the outer sheath and remove it from the body. The procedure can be repeated with a replacement delivery system or the stent can be reloaded on the catheter and re-used where appropriate.

With the stent partially released and properly located, the proximal end of the stent may be released as illustrated in FIG. 19. The operator pulls the pullwire 132 proximally, out of engagement with the proximal end of the stent, and the proximal end of the stent is released to expand into engagement with the prostatic urethra. When fully released, the stent will expand radially up to about 1 cm (0.4 inches) and contract longitudinally (foreshorten) to about 2.5 centimeters (one inch) in length: The actual diameter and length of the stent within the prostatic urethra will vary according to the physical condition of the prostatic urethra, the physical attributes of the stent, and the manipulation by the operator. After placement of the stent, all components of the delivery system are withdrawn from the urethra, as illustrated in FIG. 20 and the stent insertion procedure is complete.

After placement in a swollen prostate, as depicted in FIG. 20, the stent will be firmly held by the compressive forces of the prostate. The stent may be flushed with hot saline to cause the stent to heat up well above its austenite transition temperature. Of course, if the stent transition temperature is at or below body temperature, it will be sufficient to allow the stent to be heated to the austenite transition temperature by surrounding body temperature without injection of warm saline solution. The stent may be left in the urethra for some time, either as a temporary palliative for prostate ablation or it may remain in place permanently with due care taken to avoid infection.

It will be appreciated that various devices may be suitable for delivering the stent 110. Generally, a stent delivery device will advantageously enable the proximal and distal ends of the stent to be rotated relative to one another, while also providing for releasable attachment of the stent to the device. In the example given above, this is accomplished using inner and outer tubes that are rotatable relative to one another, and pullwires that connect the ends of the stent to the tubes. It will be appreciated, however, that other mechanisms may also be used to accomplish these objectives. For example, the ends of the stent could be held with an adhesive that releases the stent once it contacts a certain type of irrigation fluid or temperature.

In the embodiment described above having an inner catheter 114 and an outer catheter tube 115, a sheath 116 is provided to protect the stent during delivery. It will be appreciated, however, that the sheath 116 may not always be necessary. Moreover, a delivery device is contemplated in which the sheath 116 can be moved proximally relative to the outer catheter tube 115 to a fixed location, such that the distal end of the sheath is positioned between the proximal and distal ends of the stent. This enables the stent to be deployed partially while still retaining the stent within the device. Moreover, a device is contemplated in which the rotation of the proximal end of the stent relative to its distal end can be accurately controlled in order to prevent over or under expansion of the stent.

Figure 21:
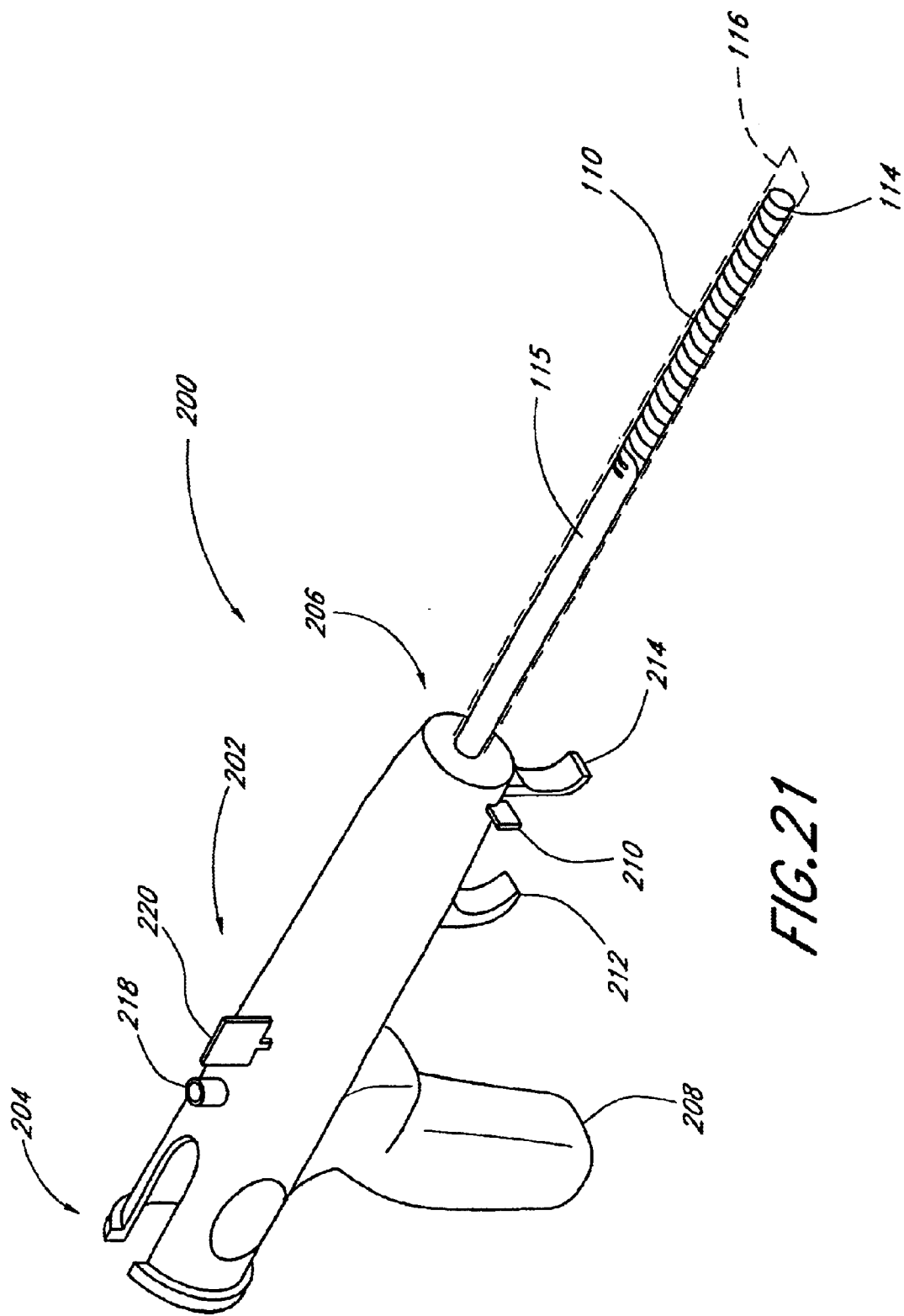
FIG. 21 is a perspective view of a stent delivery device in accordance with another embodiment of the present invention.

These and other features are provided in another example of a stent delivery device shown in FIG. 21. The delivery device 200 in one preferred embodiment includes an inner catheter 114, outer catheter tube 115 and sheath 116 as described above, each of these components being operably connected to a main body 202. The inner catheter 114 and outer catheter tube 115 releasably carry a helical stent 110 in the same manner as described above, i.e., by engaging pullwires 125 and 132 (not shown) which extend into the main body 202.

The main body 202 may include a generally cylindrical housing, extending between a proximal end 204 and a distal end 206, and includes a handle 208 by which an operator can grasp the delivery device 200. The main body further includes a retaining pin 210, described in further detail below, which prevents the sheath or first stent support 116 from moving while the pin is in place. Depending from the underside of the cylindrical body and distal to the handle 208, a control such as a pair of triggers 212 and 214 are provided, which slide within a groove (not shown) in the underside of the main body 202 for moving the sheath 116. An irrigation port 218 as described below extends from the top of the main body 202 and is in fluid communication with the inner lumen of the catheter 114. A rip cord or belt 220 connected to the outer catheter tube 115 also extends from the top of the main body 202 which, when pulled as described below, rotates the outer catheter tube 115 with respect to inner catheter 114 to partially open the stent 110.

Figure 22:
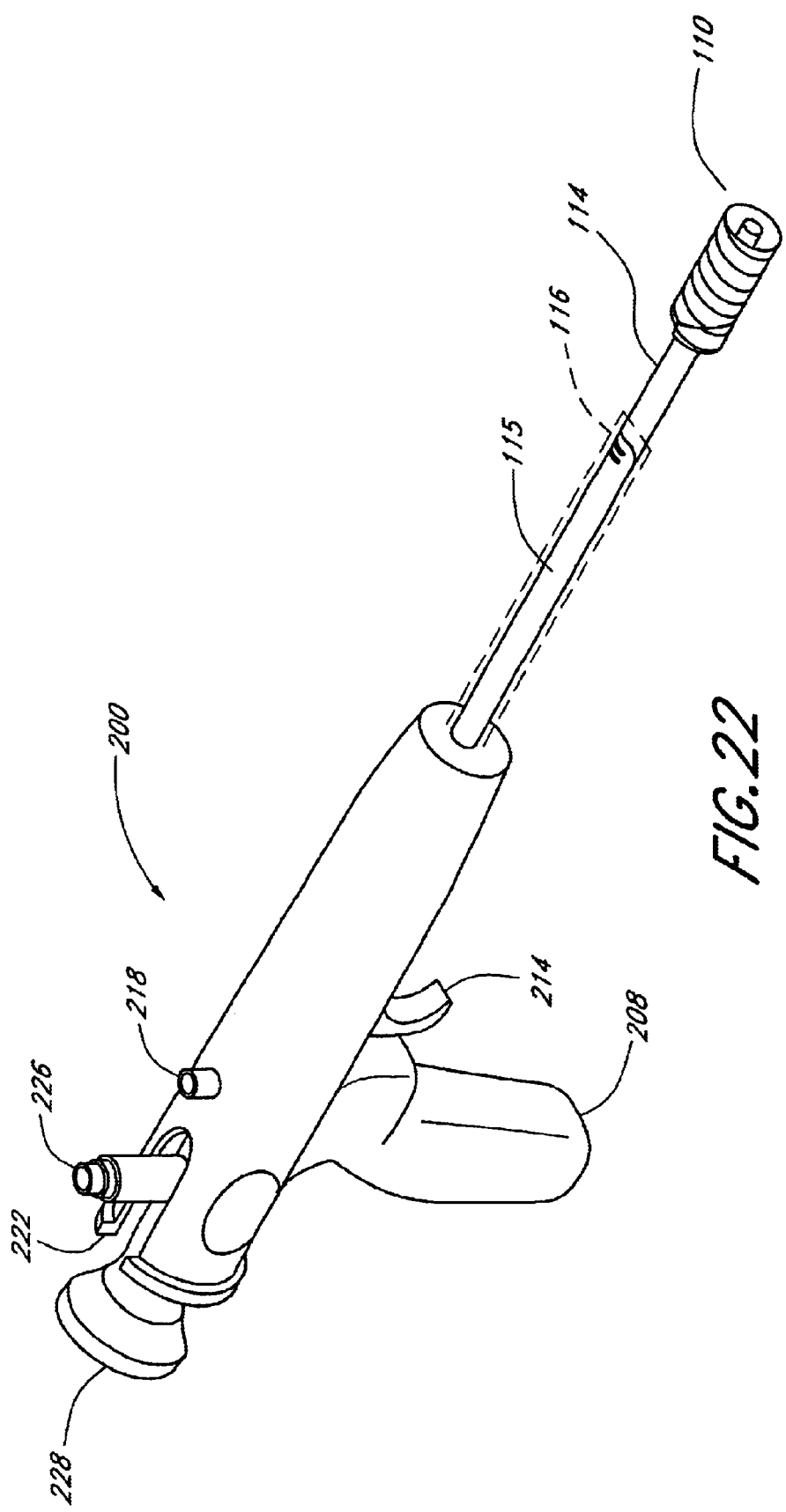
FIG. 22 is a perspective view of the stent delivery device of FIG. 21, showing the stent deployed and showing an endoscope in the proximal end of the device.

FIG. 22 illustrates the stent delivery device after the stent 110 has been deployed. As shown, at the proximal end of the main body 202, and provided within slot 222, an endoscope 224 is locked into place against the main body 202. The endoscope 224 preferably includes a first port 226 for receiving a light source and a second port 228 for visualization. The endoscope 224, when inserted into the main body 202, preferably forms a fluid tight seal therewith, on the proximal side of the irrigation port.

Figure 23:
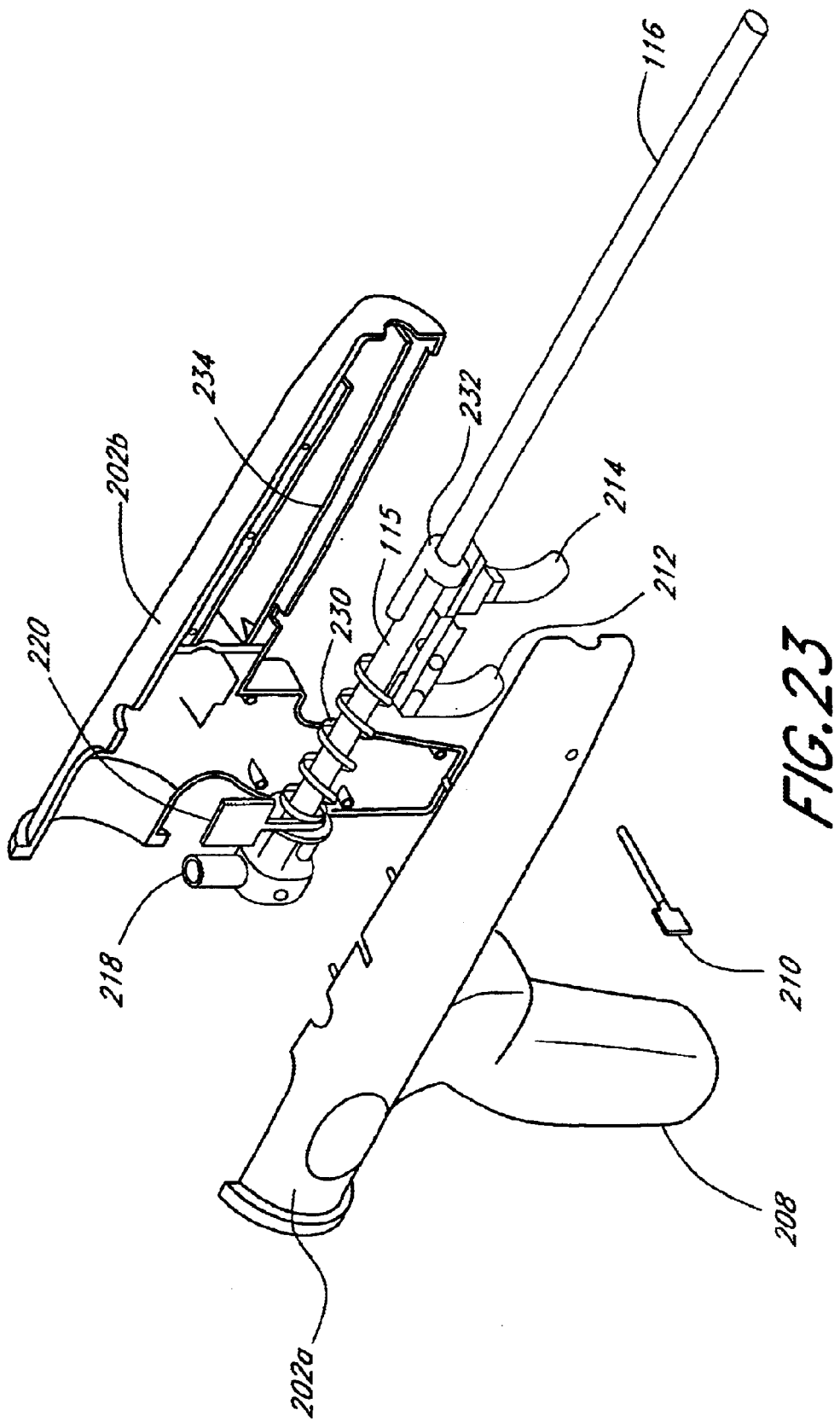
FIG. 23 is an exploded perspective view of the stent delivery device of FIG. 21.
Figure 24:
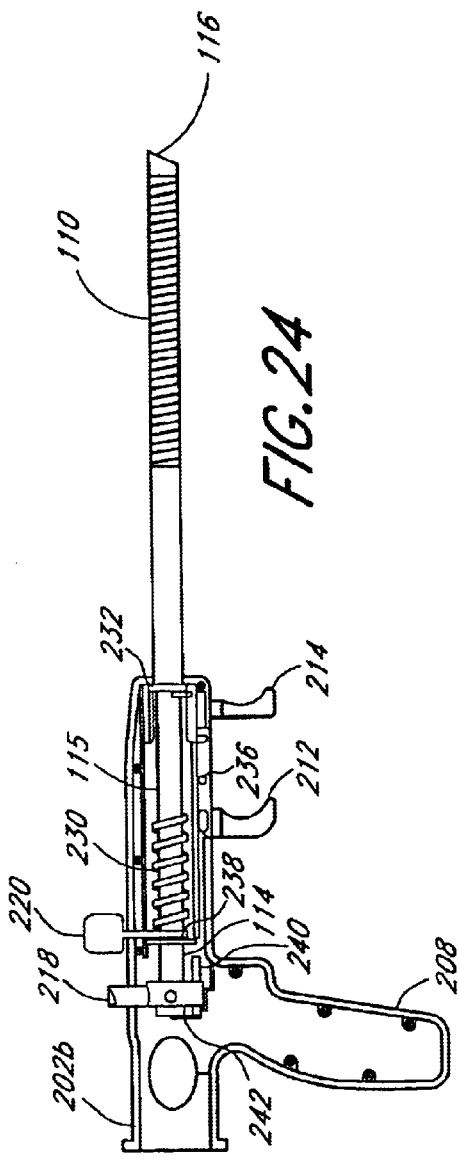
FIG. 24 is a partial cross-sectional view illustrating the interior components of the stent delivery device of FIG. 21.
Figure 25A:
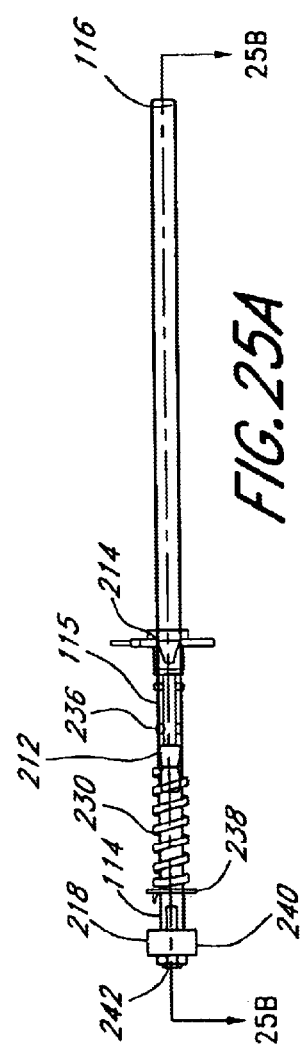
FIG. 25A is an underside view of the interior components of the stent delivery device of FIG. 21.
Figure 25B:
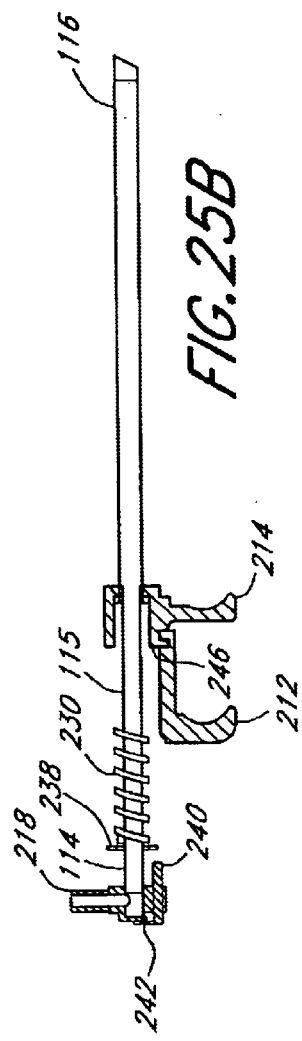
FIG. 25B is a cross-sectional view of the interior components of FIG. 25A.

FIGS. 23–25B illustrate more particularly the interior components of the stent delivery device 200. As shown in FIG. 23, the main body 202 may be formed from two halves 202a and 202b which can be secured together by screws, adhesives or other means. The sheath 116 at is proximal end is connected to an annular base 232, which slides along the outside of outer tube 115. To move the annular base 232, and thus to move sheath 116, trigger 214 engages the annular base, as shown in FIG. 25B, to move the sheath proximally. Trigger 214 preferably slides along grooves 234 provided in each of the main body halves 202a and 202b.

As shown in FIG. 25B, a second trigger 212 may be removably connected with trigger 214. When triggers 212 and 214 are in their distalmost position, trigger 212 engages trigger 214 such that they are both moveable together. As discussed above, trigger 214 slides along groove 234 in the body halves 202a and 202b, and also slides along a groove (not shown) on the underside of the main body. The trigger 212 is provided with a pin 236 which has a length which is longer than the width of the groove on the underside of the main body 202. This prevents the trigger 212 from falling out of the main body 212. When the trigger 212 is slid proximally and reaches its proximalmost point (i.e., just distal to the handle 208), the pin 236 becomes aligned with a portion of the groove on the underside of the main body which has an increased width. Upon reaching this point, the trigger 212 can be removed through the groove on the underside of the main body, thereby leaving only trigger 214 in the main body 202.

The movement of the triggers 214 and 212 proximally until the trigger 212 is removed coincides with the sheath 116 moving proximally along the stent 110 such that the distal end of the sheath is located between the proximal and distal ends of the stent. More preferably, the sheath 116 exposes approximately half of the stent secured to the inner and outer tubes. It will be appreciated that other mechanisms for limiting the proximal motion of the sheath 116 along the stent 110 may be provided.

As shown in FIG. 24, the rip cord 220 is connected to a helically wound belt 230 which is connected to the outer tube or second stent support 115. It will be appreciated that the belt can be permanently or removably attached to the outer tube 115. Thus, by pulling on the rip cord 220, the belt 230 rotates the outer tube 115 relative to the inner tube or third stent support 114. With the stent 110 connected to the inner and outer tubes as discussed above, this causes the stent 110 to expand after the sheath 116 has been removed. When the belt 230 is removably attached to the outer tube, pulling of the rip cord causes the belt 230 to disengage from the outer tube.

The belt 230 is preferably provided with a plurality of regularly spaced bumps and grooves, such that as the belt 230 is pulled away from the main body 202, the bumps indicate a fixed interval of rotation of the outer tube 115 relative to the inner catheter 114. Preferably, the length of the belt coincides with the desired amount of rotation of the outer tube 115 relative to the inner tube 114, such that the amount the stent 110 is expanded is accurately controlled.

FIGS. 24, 25A and 25B further illustrate the mechanism for removing the pullwires 125, 132 (shown above in FIG. 13) from the stent 110. Pullwire 132 of outer tube 115 at its proximal end extends through annular disc 238, which is connected to the proximal end of outer tube 115. Pullwire 132 has an enlarged portion at its proximal tip, such that movement of annular disc 238 in a proximal direction causes proximal movement of the pullwire 132. Similarly, pullwire 125 of inner tube 114 extends through a plate 242, and has an enlarged proximal tip such that movement of plate 242 in a proximal direction causes proximal movement of the pullwire 125.

After the trigger 212 and the belt 230 have been removed, the trigger 214 can be moved further proximally toward the disc 238 and plate 242. The trigger 214 has a rear surface 246 that will first contact the plate 238, moving it proximally and causing the pullwire 132 to move proximally out from the proximal end of the stent 110. The rear surface 246 then will cause the annular disc 238 to contact a rod 240 extending through the manifold 218, causing the rod 240 to slide relative to the manifold and move proximally. The proximal end of this rod will contact the plate 242 and move it proximally, and cause the pullwire 125 to release the distal end of the stent 110.

Although the embodiment described above provides for the proximal end of the stent 110 to be released prior to the distal end of the stent, it will be appreciated that the pullwires 125 and 132 could be removed simultaneously, or the pullwire 125 could be removed first at the distal end of the stent prior to removal of the pullwire 132 from the proximal end of the stent.

Figure 26:
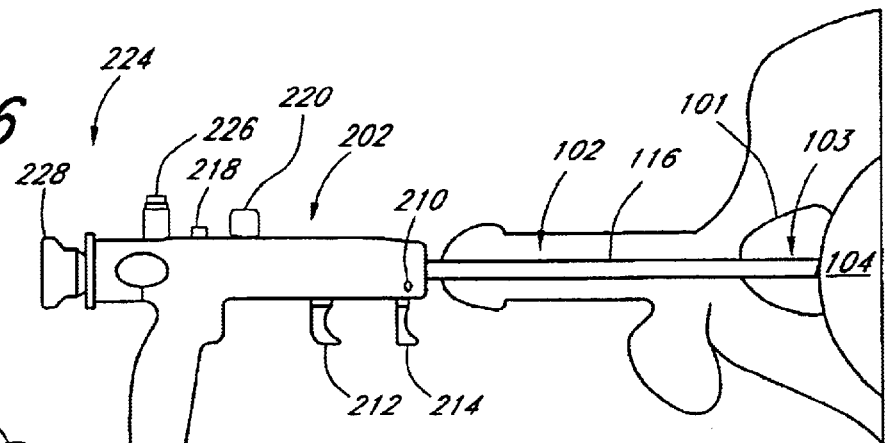
FIGS. 26–28 illustrate the use of the stent delivery device of FIG. 21 in the treatment of prostate disease.
Figure 27:
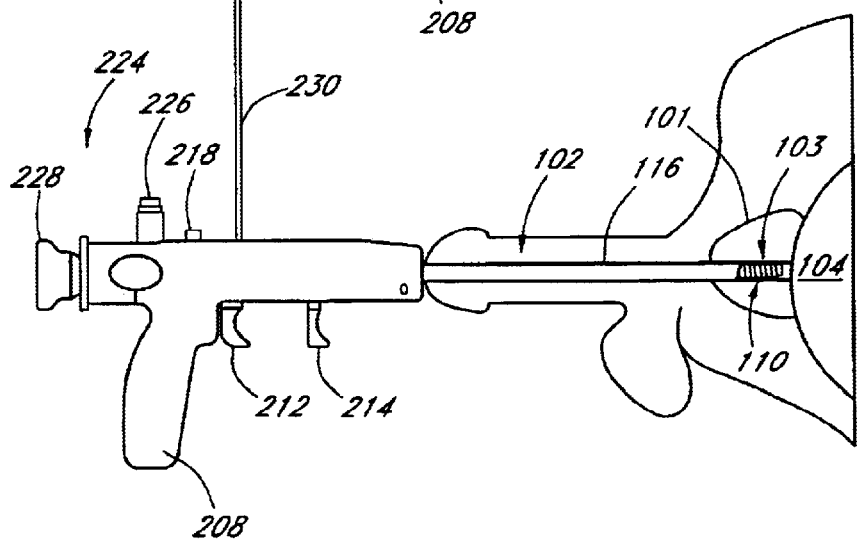
Figure 28:
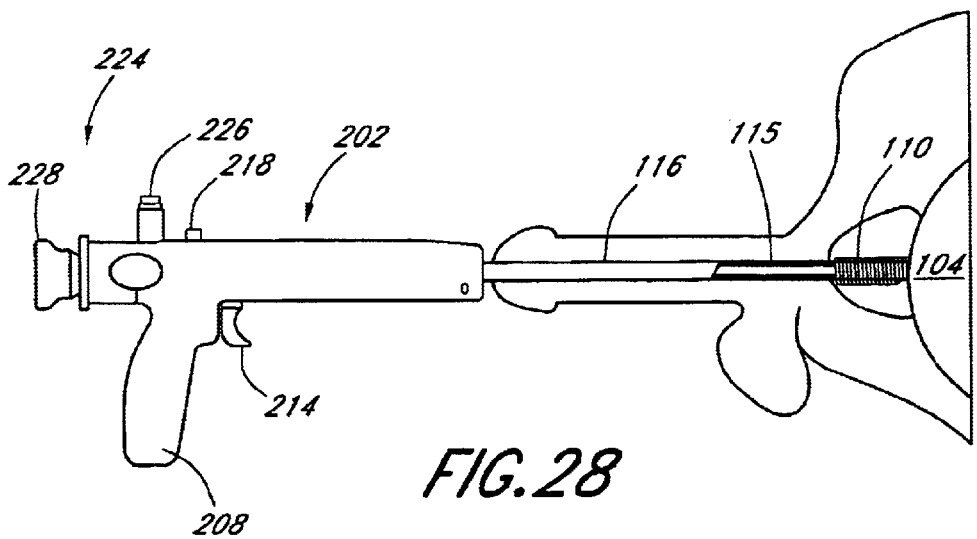

FIGS. 26–28 illustrate the operation of the device 200 according to one embodiment of the present invention and in accordance with the delivery techniques described with respect to FIGS. 15–19 above. The endoscope 224 described above is first inserted into the proximal end of the delivery device 200. The delivery system is pushed through the urethra until the stent is located in the prostatic urethra 103. Visualization using the endoscope through the lumen of the inner catheter 114 is performed so that correct initial placement may be verified visually. Once it is verified that the distal end of the stent 110 is located at the bladder neck, the locking pin 210 is removed to allow movement of the sheath 116.

In one embodiment, prior to positioning the stent 110 at the bladder neck, a room temperature irrigation solution can be connected to port 218. Preferably, water or saline can be used, which can be hung on an IV pole for gravity infusion. After removal of the locking pin 210, the room temperature irrigation solution is disconnected, and a warm irrigation solution is connected to the port 218. In one embodiment, the temperature of the solution is about 40° C., and can be pre-warmed in a warmer bottle within the operating room.

As shown in FIG. 27, pulling proximally on trigger 214 or trigger 212, the sheath 116 moves proximally relative to the inner and outer tubes 114 and 115 and relative to the stent 110 until the trigger 212 reaches its proximalmost position. At this point the sheath 116 partially exposes the stent 110, and in one embodiment, the stent is about halfway exposed. The trigger 212 can then be removed from the main body 202, as described above.

After reconfirming the stent position at the bladder neck, the rip cord 220 is pulled at least partially to pull the rotator belt up and out of the main body. The middle of the stent will thermally expand, with the distal end of the stent held in by pullwire 125, described above, and the proximal end of the stent being restrained by the sheath 116 and pullwire 132. As described above, pulling on the rip cord rotates outer tube 115 relative to inner tube 114 to expand the stent 110.

With the trigger 212 removed from the main body 202, the trigger 214 is pulled further proximally, as shown in FIG. 28, to fully expose the stent 110 from the sheath 116. As described above, proximal the motion of the trigger 214 also removes the pullwires 125 and 132 from the stent 110 to allow it deploy. The delivery device 200 is then slowly removed with care to avoid inadvertent migration of the stent. During device removal, the operator ensures that no coils of the stent extend beyond the external sphincter. If so, the operator can gently push the stent tip back into the prostatic fossa with grasping forceps.

It will be appreciated that the stent used in conjunction with the stent delivery system 200 or other delivery systems described above can have several suitable configurations. For example, the stent can have a flared ends such as shown in FIG. 7 above. Another embodiment of a suitable stent has only one flared end, as described below.

Figure 29:
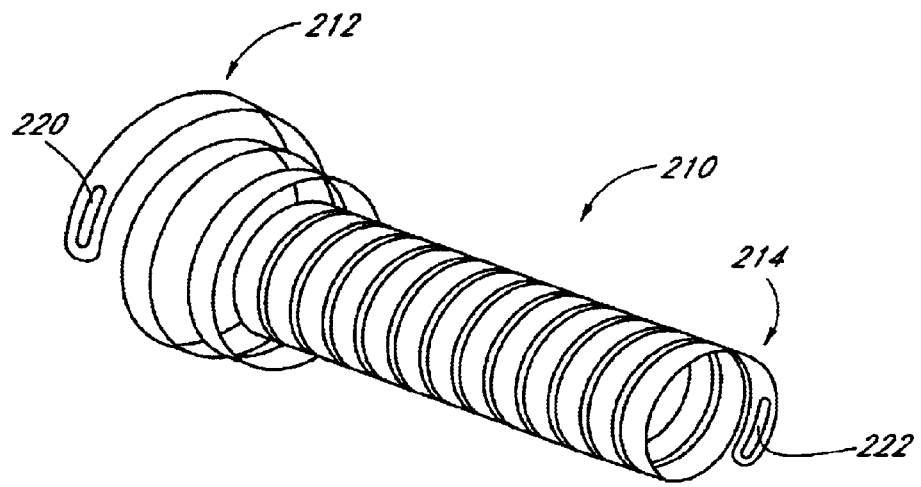
FIG. 29 is a perspective view of one embodiment of a stent suitable for delivery into the prostatic urethra of a patient.
Figure 30:
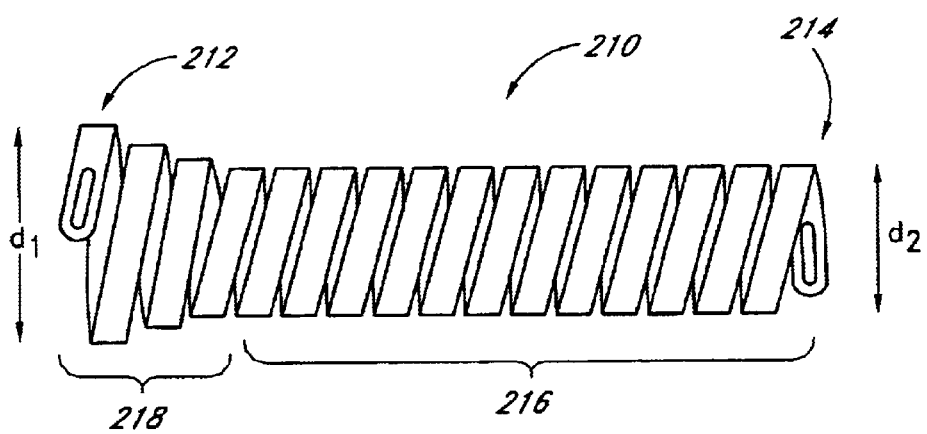
FIG. 30 is a side view of the stent of FIG. 29.
Figure 31:
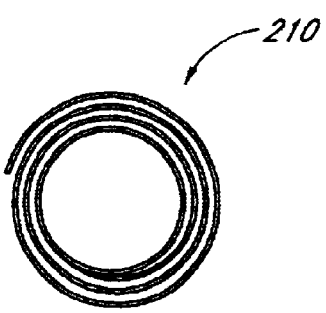
FIG. 31 is an end view of the stent of FIG. 29.

FIGS. 29–31 illustrate one embodiment of a stent 210 having only one flared or enlarged end. The stent 210 is preferably made of nitinol as described above, and is shown in FIGS. 29–31 in its expanded or austenitic state. The stent 210 has a proximal end 212, which represents the enlarged portion of the stent, and a distal end 214. The distal end 214 of the stent, when loaded onto a delivery system such as delivery system 200 of FIG. 21, is located on that portion of the delivery system farthest from the main body 202 (see FIG. 33). More particularly, the stent 210 is preferably made from a helical wire, the wire preferably having a flat or ribbon-like configuration. The successive coils of the stent 210 are closely spaced, perhaps actually touching, to prohibit intrusion of swollen prostate tissue or sloughing tissue into the prostatic urethra. Closely spaced round wire coils may also be used, and other stent configurations such as expanded metal stents, braided stents and others may also be used.

The stent 210 of FIGS. 29–31 is expandable between a collapsed shape and an expanded shape. In one embodiment, the collapsed shape of the stent refers to the condition when the stent is cooled into its martensite state and deformed to mount onto a delivery catheter such as delivery system 200 above. The expanded shape refers to the austenitic state of the stent after the stent has been heated to assume its memorized shape. In another embodiment, the collapsed shape may also refer to a martensitic condition which is stress-induced, with the expanded shape referring to the austentic state when the stress is removed and the stent returns to its memorized shape. It will be appreciated, however, that the stent need not be made of a shape memory or superelastic material, and thus can be made to be collapsible and expandable by other mechanisms as well.

The stent 210 illustrated in FIG. 30 preferably has a substantially cylindrical, constant diameter shape from its distal end 214 over a majority of the length of the stent. In one embodiment, where the overall length of the expanded stent is about 3 to 7 cm, more preferably about 4 cm, the stent is substantially cylindrical in a region 216 over a length of about 2 to 6 cm, more preferably about 3 cm. The stent also includes an enlarged region 218 which in one embodiment is about 1 cm long, wherein the outer diameter of the expanded stent progressively increases toward its proximal end 212. This progressively increasing outer diameter can be considered to be trumpet-shaped, and may increase in a linear or non-linear fashion as described below. In a preferred embodiment, this enlarged region corresponds to about three turns of the helical stent. The expanded stent preferably has a diameter $d_1$ at its proximal end 212 of about 1 to 3 cm, more preferably about 1.4 cm, and a diameter $d_2$ at its distal end 214 preferably less than about 1 cm, more preferably about 0.6 to 1 cm, and even more preferably about 0.8 cm.

In one embodiment, the enlarged region 218 gradually curves outward such that the increase in diameter of the stent at its proximal end is non-linear and the proximal end. Other embodiments are also contemplated wherein the outer diameter at the proximal end increases in a linear manner. In one preferred embodiment, the angle defined between the start of the enlarged region and the outermost point of the stent at the proximal end, with respect to the longitudinal axis of the stent, is about 10–45 degrees, more preferably about 15–30 degrees, and even more preferably about 20 degrees.

Figure 32:
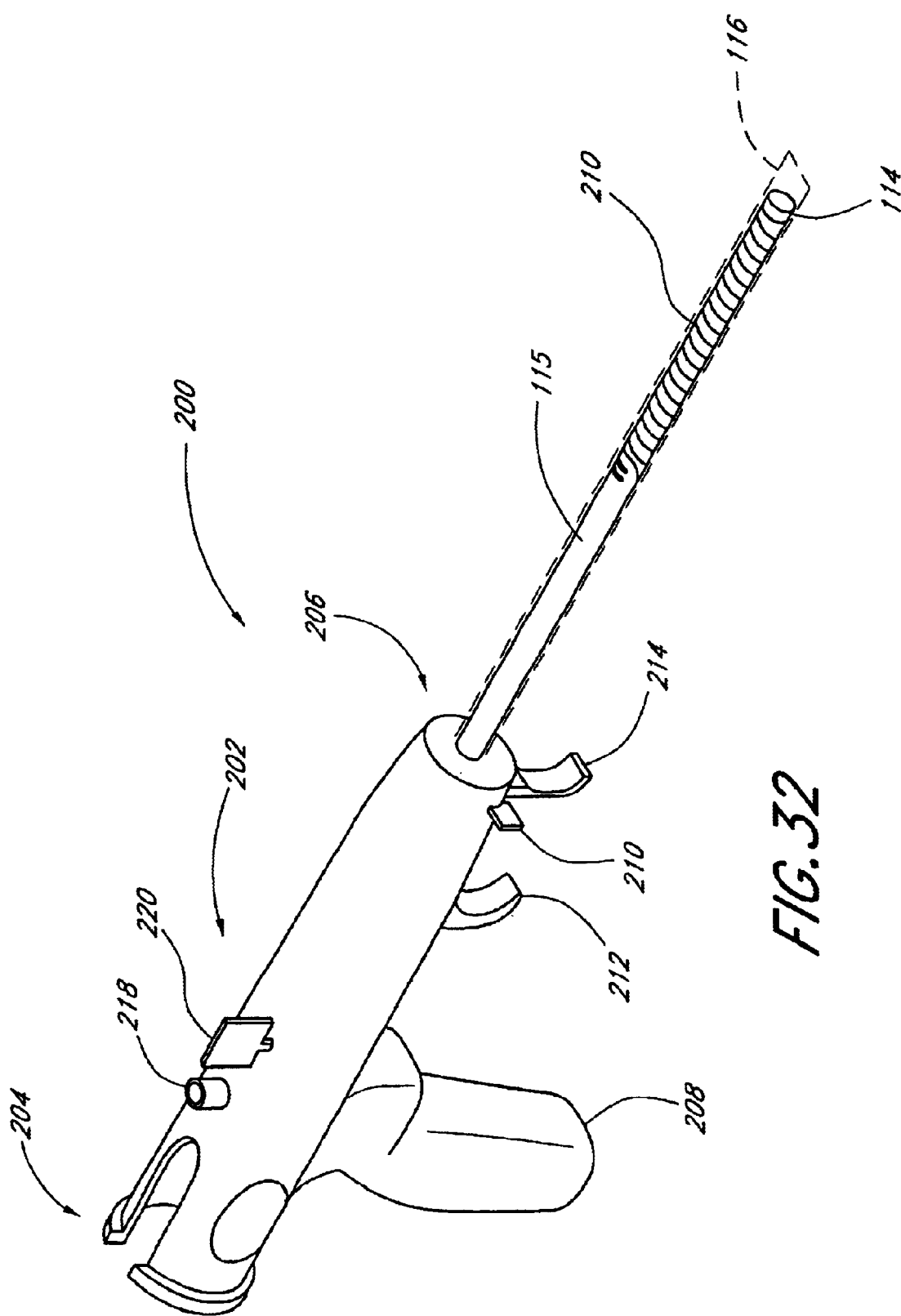
FIG. 32 is a perspective view of the stent of FIG. 29 mounted on a suitable delivery system prior to expansion of the stent.

The stent 210 described above is preferably delivered into the prostatic urethra of a patient using a delivery device similar to the device 200 described above. The stent 210 includes apertures 220 and 222 for receiving pullwires 132 and 125, respectively, described above. FIG. 32 illustrates a device 200 having a stent 210 located thereon prior to expansion of the stent. The stent is preferably tightly wound over the inner catheter into its collapsed shape, with the pullwire 125 (not shown) of inner catheter 114 engaging the distal end of the stent 210, and the pullwire 132 (not shown) of outer catheter 115 engaging the proximal end of the stent 210. When in its collapsed state, the stent 210 preferably has a substantially cylindrical outer diameter due to being restrained by the inner catheter 114, the outer catheter 115 and the sheath 116. This restrained outer diameter is preferably sufficiently small to enable the stent 210 to fit into the prostatic urethra of a patient.

Figure 33:
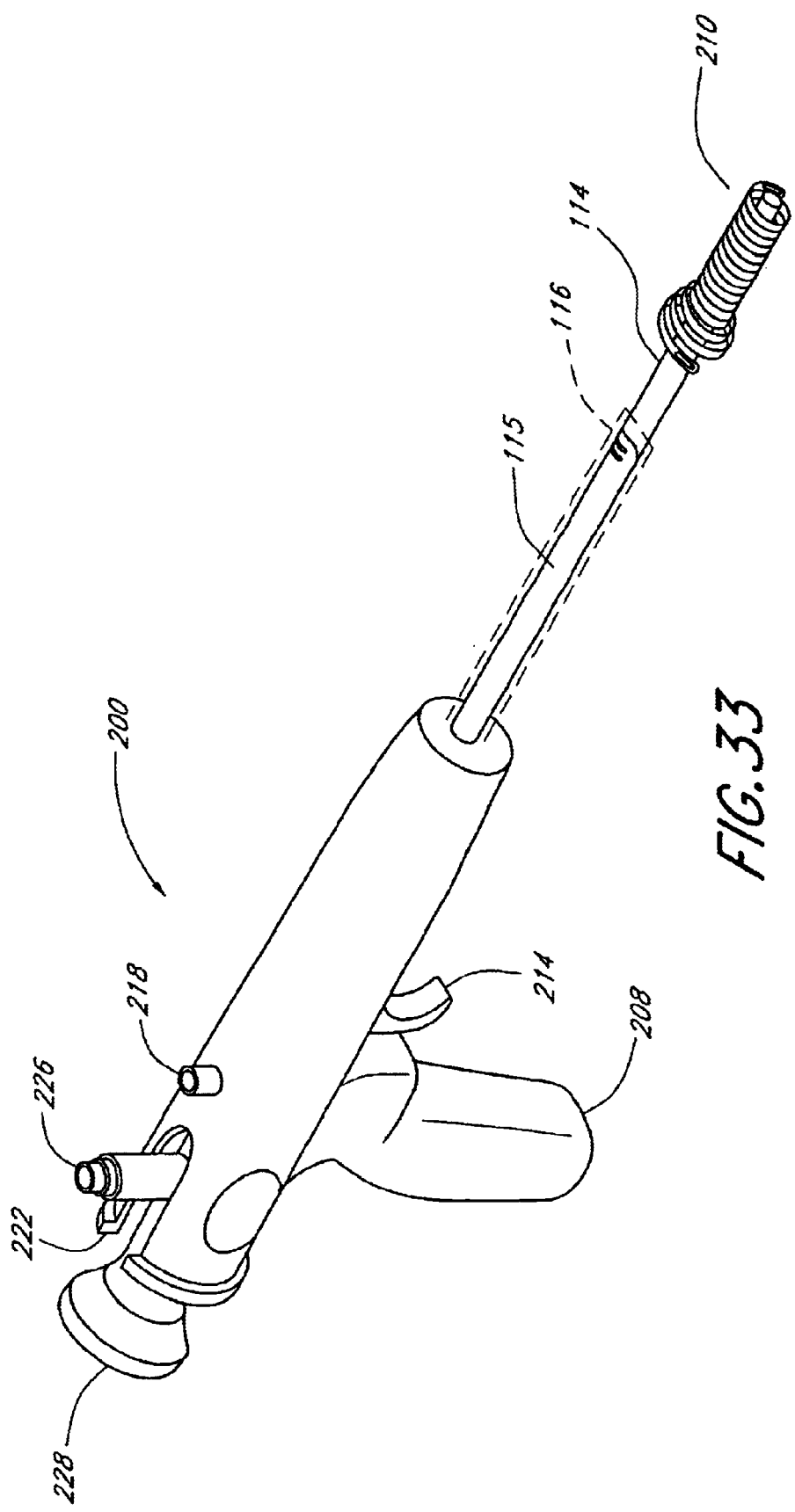
FIG. 33 is a perspective view of the stent of FIG. 29 mounted on a suitable delivery system after expansion of the stent.
Figure 34:
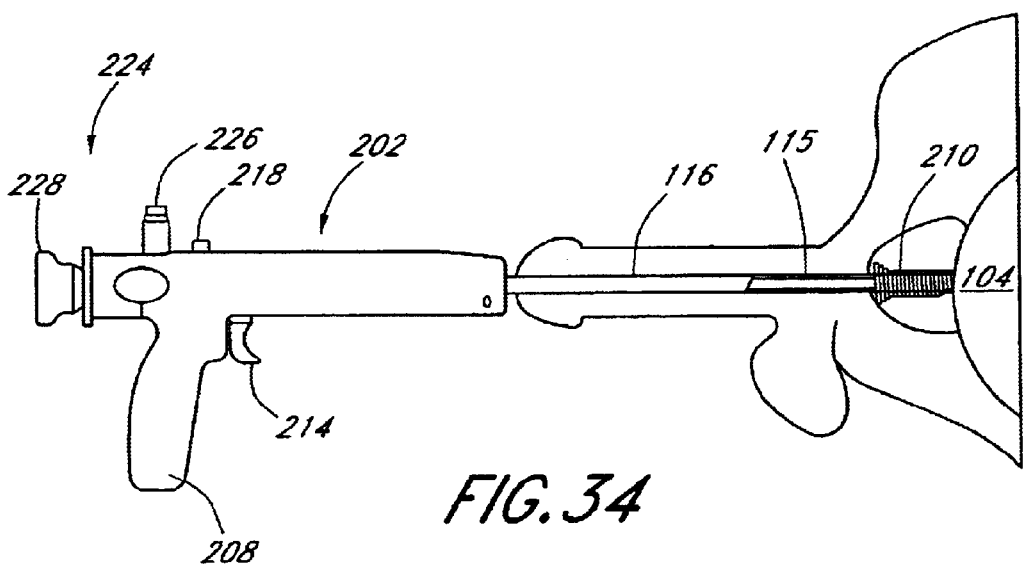
FIG. 34 illustrates the use of the stent delivery device of FIG. 32 in the treatment of prostate disease.

The stent 210 is preferably delivered using the delivery device 200 in the same manner as the delivery of stent 110 described above. FIG. 33 illustrates schematically the delivery device 210 after the sheath 116 has been retracted and the pullwires 125 and 132 have been removed to release the stent 210 into the prostatic urethra. As illustrated in FIG. 34, when the stent is delivered to the prostatic urethra, the distal end of the stent is preferably aligned with the bladder neck or about 0.25 cm short of the bladder neck.

The preferred embodiment of the stent 210 illustrated in FIGS. 29–31 preferably has only one enlarged or flared end. This design advantageously prevents migration of the stent within the prostatic urethra, even as compared to designs having two flared ends (such as illustrated in FIG. 7). This is because when a design with two flared ends is employed, the muscle at the bladder neck sphincter 105 can grab hold of the flared distal end of the stent and cause migration of the stent into the bladder. By utilizing only one flared end on the proximal end of the device, the distal end of the stent has a uniform outer diameter that is less susceptible to being moved by the bladder neck sphincter. In addition, the enlarged proximal end assists in holding the stent in position. In particular, because the proximal end of the stent has a progressively increasing diameter, the stent is better able to secure itself within the prostatic urethra and prevent migration toward the bladder. This design particularly is an improvement over the design of Othel-Jacobsen, wherein the larger diameter portion of the stent has a constant diameter which is less effective in preventing migration.

Furthermore, as described above, the diameter of the stent 210 in its constant diameter region 216 is preferably small to prevent migration of the stent into the bladder. When a larger diameter stent is used, the muscle at the bladder neck sphincter can more easily grab hold of the stent and move it towards the bladder. Thus, the smaller diameter of the stent, preferably less than about 1 cm, prevents this from happening.

The diameter at the very proximal end of the stent is preferably about 25% or more larger than the diameter of the stent in cylindrical region 216, more preferably about 50% or more larger, and even more preferably about 75% or more larger. This large ratio between the diameters at the proximal end and the distal end of the stent enables the stent to be secured more firmly in the prostatic urethra to prevent stent migration.

While the preferred embodiments of the devices and methods have been described, they are merely illustrative of the principles of the invention. Other embodiments and configurations may be devised without departing from the spirit of the inventions and the scope of the appended claims. While the inventions have been described in the environment of urology, the application of the inventive concepts in other areas of heat therapy and temporary stent application will be beneficial. It is specifically contemplated that the materials employed in the illustrated embodiments be improved upon, that methods and patterns of irradiation and heating of the stent be improved upon, and that the time tables for therapy discussed above be improved upon, and that all such improvements fall within the scope of the claims.

What is claimed is:

1. A stent for use within the pro static urethra, said stent comprising:

a length of wire having a substantially helical configuration and being expandable between a collapsed shape and an expanded shape, said expanded shape including a proximal end and a distal end and a substantially cylindrical portion with a substantially constant diameter extending from the distal end over multiple complete turns toward the proximal end, and an enlarged region proximal of the cylindrical portion wherein an outer diameter of the enlarged region progressively increases toward the proximal end over at least two complete turns:

wherein the wire has a substantially helical configuration from its proximal end continuously to its distal end.

2. The stent of claim 1, wherein the wire is flat.

3. The stent of claim 1, wherein the diameter of the stent in its cylindrical portion is less than about 1 cm.

4. The stent of claim 1, wherein the diameter of the stent in its cylindrical portion is about 0.6 to about 1 cm.

5. The stent of claim 1, wherein the diameter of the stent at its proximal end is about 25% or more larger than the diameter of the stent in its cylindrical portion.

6. The stent of claim 1, wherein the diameter of the stent at its proximal end is about 50% or more larger than the diameter of the stent in its cylindrical portion.

7. The stent of claim 1, wherein the diameter of the stern at its proximal end is about 75% or more larger than the diameter of the stent in its cylindrical portion.

8. The stent of claim 1, wherein the stent is enlarged only at its proximal end.

9. The stent of claim 1, wherein the wire is made of a shape memory material.

10. The stent of claim 9, wherein the wire is superelastic.

11. The stent of claim 9, wherein the wire is made of nitinol.

12. The stent of claim 1, wherein the expanded shape corresponds to a high temperature austenite state and the collapsed shape corresponds to a low temperature martensite state.

13. The stent of claim 12, wherein the high temperature austenite state is achieved upon heating to a temperature range of about 38–60° C., and the low temperature martensite state is achieved upon cooling to the temperature range of about 30–35° C.

14. A method for delivering a stent into the prostatic urethra of a patient, the method comprising:

providing a length of wire having a substantially helical configuration and being expandable between a collapsed shape and an expanded shape, said expanded shape including a proximal end and a distal end and a substantially cylindrical portion extending from the distal end toward the proximal end, and an enlarged region proximal of the cylindrical portion wherein an outer diameter of the enlarged region progressively increases toward the proximal end;

delivering the stent in its collapsed shape into the prostatic urethra of the patient; and expanding the stent to its expanded shape within the prostatic urethra of the patient, wherein the proximal end of the stent is located relatively closer to the external sphincter and the distal end of the stent is located relatively closer to the bladder neck sphincter.

15. The method of claim 14, wherein the wire is flat.

16. The method of claim 14, wherein the diameter of the stent in its cylindrical portion is less than about 1 cm.

17. The method of claim 14, wherein the diameter of the stent in its cylindrical portion is about 0.6 to about 1 cm.

18. The method of claim 14, wherein the diameter of the stent at its proximal end is about 25% or more larger than the diameter of the stent in its cylindrical portion.

19. The method of claim 14, wherein the diameter of the stent at its proximal end is about 50% or more larger than the diameter of the stent in its cylindrical portion.

20. The method of claim 14, wherein the diameter of the stent at its proximal end is about 75% or more larger than the diameter of the stent in its cylindrical portion.

21. The method of claim 14, stent of claim 1, wherein the wire is made of a shape memory material.

22. The method of claim 21, wherein the expanded shape corresponds to a high temperature austenite state and the collapsed shape corresponds to a low temperature martensite state.

23. The method of claim 22, wherein the stent is collapsed in its low temperature martensite state.

24. The method of claim 22, wherein the stent is expanded in its high temperature austenite state.

* * * * *